(12) United States Patent
Kishida et al.

(10) Patent No.: US 12,227,604 B2
(45) Date of Patent: Feb. 18, 2025

(54) METHOD FOR PRODUCING ORGANIC SULFUR COMPOUND, CARRIER, METHOD FOR PRODUCING SAID CARRIER, LIGAND-IMMOBILIZING CARRIER, CHROMATOGRAPHY COLUMN, AND METHOD FOR DETECTING OR ISOLATING TARGET SUBSTANCE

(71) Applicant: JSR CORPORATION, Minato-ku (JP)

(72) Inventors: Takanori Kishida, Minato-ku (JP); Takaya Nishida, Minato-ku (JP)

(73) Assignee: JSR CORPORATION, Minato-ku (JP)

( * ) Notice: Subject to any disclaimer, the term of this patent is extended or adjusted under 35 U.S.C. 154(b) by 862 days.

(21) Appl. No.: 17/291,304

(22) PCT Filed: Nov. 6, 2019

(86) PCT No.: PCT/JP2019/043553
§ 371 (c)(1),
(2) Date: May 5, 2021

(87) PCT Pub. No.: WO2020/095963
PCT Pub. Date: May 14, 2020

(65) Prior Publication Data
US 2022/0001358 A1    Jan. 6, 2022

(30) Foreign Application Priority Data

Nov. 6, 2018 (JP) .................................. 2018-208850
Nov. 6, 2018 (JP) .................................. 2018-208851

(51) Int. Cl.
| | | |
|---|---|---|
| C08F 228/04 | (2006.01) |
| B01D 15/20 | (2006.01) |
| B01D 15/38 | (2006.01) |
| B01J 20/26 | (2006.01) |
| B01J 20/281 | (2006.01) |
| B01J 20/285 | (2006.01) |

(Continued)

(52) U.S. Cl.
CPC ............ *C08F 228/04* (2013.01); *B01D 15/20* (2013.01); *B01D 15/3809* (2013.01); *B01J 20/267* (2013.01); *B01J 20/281* (2013.01); *B01J 20/285* (2013.01); *B01J 20/3085* (2013.01); *C07C 323/12* (2013.01); *C07D 327/00* (2013.01); *C07K 1/22* (2013.01); *C07K 14/765* (2013.01); *C07K 16/32* (2013.01); *C08F 8/34* (2013.01); *C08F 220/325* (2020.02); *C12N 9/2462* (2013.01); *C12Y 302/01017* (2013.01); *G01N 33/545* (2013.01); *C07K 2317/24* (2013.01); *C07K 2317/76* (2013.01); *C07K 2319/30* (2013.01)

(58) Field of Classification Search
None
See application file for complete search history.

(56) References Cited

U.S. PATENT DOCUMENTS

| | | |
|---|---|---|
| 3,501,514 A | 3/1970 | Grimm et al. |
| 2006/0020144 A1 | 1/2006 | Lal et al. |

(Continued)

FOREIGN PATENT DOCUMENTS

| | | |
|---|---|---|
| CN | 102834407 A | 12/2012 |
| JP | 9-302029 A | 11/1997 |

(Continued)

OTHER PUBLICATIONS

Chinese Office Action and Search Report issued Jan. 5, 2023 in Chinese Application 201980071983.9, (with unedited computer generated English translation), 27 pages.
Extended European Search Report issued Jul. 25, 2022, for European Patent Application No. 19881620.9, 9 pages.
Kishida Takanori, et al., "Efficient linking of two epoxides using potassium thioacetate in water and its use in polymerization", Chemical Communications, vol. 58, No. 8, Jan. 25, 2019, pp. 1108-1110, XP55942804.
John Brittain, et al., "Triphenylsilanethiol: A solid H2S equivalent in the ring opening of epoxides", Tetrahedron Letters vol. 34, No. 21, May 21, 1993, pp. 3363-3366, XP026636858.
International Search Report issued Feb. 4, 2020 in PCT/JP2019/043553, 4 pages.
A.H. Williams et al., "New Organic Sulphur Vesicants. Part II. Analogues of 2: 2'Dichlorodiethyl Sulphide and 2: 2'-Di-(2-chloroethylthio)diethyl Ether", Journal of the Chemical Society, (1948) pp. 41, 5 pages.

(Continued)

*Primary Examiner* — Marc S Zimmer
(74) *Attorney, Agent, or Firm* — Oblon, McClelland, Maier & Neustadt, L.L.P.

(57) ABSTRACT

A carrier which may have excellent pressure resistance, and even when a protein ligand is not immobilized thereon, a high dynamic binding capacity to a target substance, and a high performance of separating a target substance from a biological sample. Such a carrier may include a polymer having a crosslinked structure containing a divalent group of formula (1):

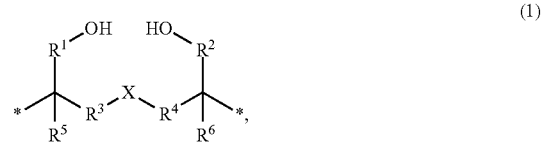

(1)

wherein $R^1$ to $R^4$ are independently a single bond or divalent hydrocarbon group, $R^5$ and $R^6$ are independently H or a hydrocarbon group, X is a thio group, sulfinyl group, sulfonyl group, oxy group, $>N(\text{—}R^{31})$, $>Si(\text{—}R^{32})_2$, $>P(\text{—}R^{33})$, $>P(=O)(\text{—}R^{34})$, $>B(\text{—}R^{35})$, or $>C(\text{—}R^{36})_2$ ($R^{31}$ to $R^{36}$ independently being H or hydrocarbon group), and * is a bond, provided that when both $R^1$ and $R^3$ or both $R^2$ and $R^4$ are a divalent hydrocarbon group, respectively, $R^1$ and $R^3$ or $R^2$ and $R^4$ may form a ring together with an adjacent carbon atom.

9 Claims, No Drawings

(51) Int. Cl.
*B01J 20/30* (2006.01)
*C07C 323/12* (2006.01)
*C07D 327/00* (2006.01)
*C07K 1/22* (2006.01)
*C07K 14/765* (2006.01)
*C07K 16/32* (2006.01)
*C08F 8/34* (2006.01)
*C08F 220/32* (2006.01)
*C12N 9/36* (2006.01)
*G01N 33/545* (2006.01)

(56) References Cited

U.S. PATENT DOCUMENTS

| 2006/0128995 A1 | 6/2006 | Wang et al. |
| 2017/0043320 A1 | 2/2017 | Momiyama et al. |

FOREIGN PATENT DOCUMENTS

| JP | 2003-511659 A | 3/2003 |
| JP | 2006-111717 A | 4/2006 |
| JP | 2009-503203 A | 1/2009 |
| JP | 2009-91503 A | 4/2009 |
| JP | 5250985 B2 | 4/2013 |
| JP | 2016-50897 A | 4/2016 |
| WO | WO 2005/010529 A1 | 2/2005 |
| WO | WO 2015/119255 A1 | 8/2015 |

OTHER PUBLICATIONS

Najmedin Azizi et al., "Simple and highly efficient catalyst- and waste-free ring opening of epoxides with $Na_2S$ in water", Monatsh Chem, vol. 141, 2010, pp. 323-326.

Isao Ikeda et al., "Synthesis of Dihydroxy Thia Crown Ethers and Derivatization to Bicyclic Crown Compounds", Journal of Organic Chemistry, 1986, 51, pp. 1128-1130.

Chi-Huey Wong et al., "Recombinant 2-Deoxyribose-5-phosphate Aldolase in Organic Synthesis: Use of Sequential Two- Substrate and Three-Substrate Aldol Reactions", Journal of the American Chemical Society, 1995, vol. 117, No. 12, pp. 3333-3339.

Svein Ore et al., "Cyclic Compounds from the Reaction of Bisphenol A Diglycidyl Ether with Amines", Acta Chemica Scandinavica, 1970, vol. 24, No. 7, pp. 2397-2407.

METHOD FOR PRODUCING ORGANIC SULFUR COMPOUND, CARRIER, METHOD FOR PRODUCING SAID CARRIER, LIGAND-IMMOBILIZING CARRIER, CHROMATOGRAPHY COLUMN, AND METHOD FOR DETECTING OR ISOLATING TARGET SUBSTANCE

CROSS-REFERENCE TO RELATED APPLICATIONS

The present application is the national stage of international application PCT/JP2019/043553, filed on Nov. 6, 2019, and claims the benefit of the filing date of Japanese Appl. No. 2018-208850, filed on Nov. 6, 2018, and Japanese Appl. No. 2018-208851, filed on Nov. 6, 2018.

TECHNICAL FIELD

The present invention relates to a method for producing an organic sulfur compound, a carrier, a method for producing the carrier, a ligand-immobilized carrier, a chromatography column, and a method for detecting or isolating a target substance. More specifically, the present invention relates to a method for producing an organic sulfur compound, an organic sulfur compound obtained by the production method, a carrier, a method for producing the carrier, a ligand-immobilized carrier, a chromatography column, and a method for detecting or isolating a target substance.

BACKGROUND ART

There are various kinds of organic sulfur compounds such as sulfides, sulfoxides, and sulfones, regardless of whether they are high molecular weight compounds or low molecular weight compounds. Such organic sulfur compounds tend to have properties such as hydrophilization action, antifouling action, molecular recognition ability, and stimulus responsiveness, and are utilized in a wide range of fields, for example, carriers for antibody purification, surface treatments, and biomaterial production. Among the above organic sulfur compounds, a sulfoxide and a sulfone are generally produced by oxidation of a sulfide (for example, Patent Literatures 1 and 2).

As a method for producing a sulfide, for example, it is known that a method in which hydrogen sulfide, sodium sulfide, or sodium hydrogen sulfide is used to ring-open two cyclic ether groups (for example, an epoxy group) and a thio group is introduced therebetween (Non-Patent Literatures 1 to 3). According to the method, it is possible to obtain a compound having a plurality of hydroxyl groups and thio groups derived from a cyclic ether group.

However, since hydrogen sulfide is combustible and flammable, and further is highly toxic, its use is greatly restricted. Sodium sulfide and sodium hydrogen sulfide also have a problem related to safety, for example, have a self-heating property, cause for example, inflammation and pain in the eyes and skin, and since the aqueous solution is strongly alkaline, may generate hydrogen sulfide during the neutralization treatment.

Meanwhile, in the field of biopharmaceuticals represented by for example, antibody pharmaceuticals, techniques for expressing target substances such as proteins have been remarkably progressed, and consequently it is required by an improvement in productivity in the isolation step by for example, chromatography. As a method for improving productivity, it includes that the concentration of impurities mixedly present in a pharmaceutical raw material can be reduced as much as possible by one isolation, and the number of purifications and the number of steps can be reduced accordingly. It leads to an increase in demand for a carrier which can achieve this.

Then, in order to improve the efficiency of removing impurities in isolation of a target protein, a technique for hydrophilizing a carrier has been reported (Patent Literature 3). The following is known as the carrier for hydrophilization: a specific solid phase carrier in which the inside of micropores is fixed by a water-soluble polymer (Patent Literature 4), a solid phase carrier formed by subjecting a hydrophilic monomer such as an acrylamide monomer to reverse phase suspension polymerization, and a solid phase carrier obtained by subjecting a hydrophilic monomer to hydrophobization by, for example, a protecting group, polymerization, and then deprotection (Patent Literatures 5 to 7).

However, when the antifouling property of the carrier is improved by the above hydrophilization technique, there is a problem that for example, pressure resistance is lowered.

Therefore, as a carrier having improved pressure resistance, a carrier having a crosslinked structure introduced using 3,6-dioxa-1,8-octanedithiol has been proposed (Patent Literature 1).

CITATION LIST

Patent Literature

Patent Literature 1: WO 2015/119255 A
Patent Literature 2: JP 2016-50897 A
Patent Literature 3: WO 2005/010529 A
Patent Literature 4: JP 5250985 B2
Patent Literature 5: JP 2003-511659 A
Patent Literature 6: JP 2009-503203 A
Patent Literature 7: JP 2006-111717 A

Non-Patent Literature

Non-Patent Literature 1: Journal of the Chemical Society, (1948) p. 41
Non-Patent Literature 2: Monatshefte fur Chemie, vol. 141, nb. 3, (2010) p. 323-326
Non-Patent Literature 3: Journal of Organic Chemistry, 1986, 51, p. 1128-1130

SUMMARY OF INVENTION

Technical Problem

The present invention is to provide a noble means capable of producing an organic sulfur compound safely, efficiently, and by a simple operation, the production of an organic sulfur compound including a step of ring-opening two cyclic ether groups to introduce a thio group therebetween.

Meanwhile, the carrier described in Patent Literature 1 has been used exclusively for isolating a target protein after immobilizing a protein ligand such as protein A. In general, in order to efficiently capture a target substance, it is necessary to immobilize a protein ligand depending on the kind of target substance. In fact, when the present inventors used a carrier crosslinked with 3,6-dioxa-1,8-octanedithiol without immobilizing a protein ligand for isolating an antibody, the antibody was eluted in a stage of washing the carrier, and consequently could not be separated well.

Then, when a target substance was separated from a biological sample using a carrier on which the protein ligand was immobilized, the protein ligand sometimes leaked from the carrier and was mixed into the target substance. Such mixing of the protein ligand is particularly problematic when separating a substance requiring high purity, such as an antibody drug. Further, there is a problem that the number of unit operations is increased, which causes high cost.

Therefore, the present invention is to provide a carrier which has excellent pressure resistance, and even when a protein ligand is not immobilized thereon, has a high dynamic binding capacity to a target substance, and has a high performance of separating a target substance from a biological sample.

Solution to Problem

The present inventors attempted to add a thiocarboxylic acid to a cyclic ether group-containing compound and allow to react. To such attempt, they did not observe formation of a desired sulfide (a compound in which a thio group is introduced between two divalent groups formed by ring-opening the cyclic ether group).

Then as a result of intensive studies of the present inventors, they found that when a cyclic ether group-containing compound is reacted with a thiocarboxylate, a thio group is introduced between two divalent groups formed by ring-opening a cyclic ether group and consequently an organic sulfur compound can be produced safely, efficiently, and by a simple operation, thereby completing the present invention.

That is, the present invention provides the following <1> to <3>.

<1> A method for producing a compound containing a divalent group represented by the following Formula (21), the method including reacting a cyclic ether group-containing compound with a thiocarboxylate (hereinafter, also referred to as "method for producing an organic sulfur compound of the present invention"):

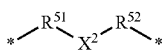
(21)

wherein
$R^{51}$ and $R^{52}$ independently represent a divalent group formed by ring-opening a cyclic ether group,
$X^2$ represents a thio group, a sulfinyl group, or a sulfonyl group, and
* represents a bond.

<2> A compound containing a divalent group represented by Formula (21), obtained by the production method described in <1>.

<3> A compound represented by the following Formula (β) (hereinafter, also referred to as "compound (β) of the present invention"):

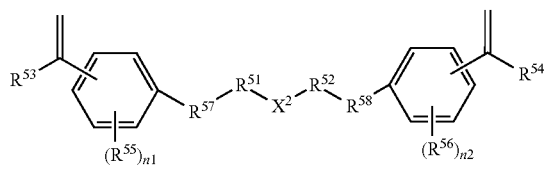
(β)

wherein
$R^{51}$ and $R^{52}$ independently represent a divalent group formed by ring-opening of a cyclic ether group,
$R^{53}$ and $R^{54}$ independently represent a hydrogen atom or a methyl group,
$R^{55}$ and $R^{56}$ independently represent a halogen atom or an organic group,
$R^{57}$ and $R^{58}$ independently represent a single bond or a divalent linking group,
$X^2$ represents a thio group, a sulfinyl group, or a sulfonyl group, and
n1 and n2 independently represent an integer from 0 to 4.

In addition, as a result of intensive studies of the present inventors, the present inventors have found that a carrier including a polymer having a crosslinked structure containing a specific divalent group has excellent pressure resistance, and even when a protein ligand is not immobilized thereon, has a high dynamic binding capacity to a target substance and a high performance of separating a target substance from a biological sample, thereby completing the present invention.

That is, the present invention also provides the following <4> to <9>.

<4> A carrier including a polymer having a crosslinked structure containing a divalent group (hereinafter, also referred to as "specific crosslinked structure") represented by the following Formula (1) (hereinafter, also referred to as "carrier of the present invention"):

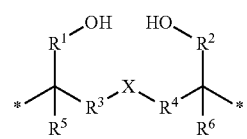
(1)

wherein
$R^1$ to $R^4$ independently represent a single bond or a divalent hydrocarbon group,
$R^5$ and $R^6$ independently represent a hydrogen atom or a hydrocarbon group,
X represents a thio group, a sulfinyl group, a sulfonyl group, an oxy group, $>N(-R^{31})$, $>Si(-R^{32})_2$, $>P(-R^{33})$, $>P(=O)(-R^{34})$, $>B(-R^{35})$, or $>C(-R^{36})_2$ ($R^{31}$ to $R^{36}$ independently represent a hydrogen atom or hydrocarbon group), and
* represents a bond,
with a proviso that when both $R^1$ and $R^3$ are a divalent hydrocarbon group, $R^1$ and $R^3$ may form a ring together with an adjacent carbon atom, and
when both $R^2$ and $R^4$ are a divalent hydrocarbon group, $R^2$ and $R^4$ may form a ring together with an adjacent carbon atom.

<5> A ligand-immobilized carrier having the carrier described in <4> and a ligand, the ligand being immobilized on the carrier (hereinafter, also referred to as "ligand-immobilized carrier of the present invention").

<6> A chromatography column in which a column container is filled with the carrier or the ligand-immobilized carrier described in <4> or <5> (hereinafter, also referred to as "chromatography column of the present invention").

<7> A method for detecting or isolating a target substance, the method including using the carrier or the ligand-immobilized carrier described in <4> or <5> (hereinafter, also referred to as "method for detecting or isolating a target substance of the present invention").

<8> A method for producing the carrier described in <4>, the method including reacting a polymer having a cyclic ether group in a molecule with a compound selected from a thiocarboxylate and a sulfanyl compound having 2 or more groups represented by the following Formula (α) in a molecule (hereinafter, also referred to as "carrier production method PR2-1 of the present invention"):

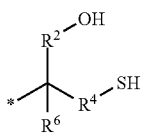

(α)

wherein $R^2$, $R^4$, $R^6$, and * are as defined above.

<9> A method for producing the carrier described in <4>, the method including the following steps B-1 and B-2 (hereinafter, also referred to as "carrier production method PR2-2 of the present invention", the carrier production method PR2-1 of the present invention and the carrier production method PR2-2 of the present invention being collectively referred to as "method for producing a carrier of the present invention"):

(Step B-1) reacting a monomer having a cyclic ether group in a molecule with a compound selected from a thiocarboxylate and a sulfanyl compound having 2 or more groups represented by the following Formula (α) in a molecule, (Step B-2) using a crosslinkable monomer obtained in step B-1 to prepare the carrier:

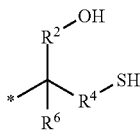

(α)

wherein $R^2$, $R^4$, $R^6$, and are as defined above.

Advantageous Effects of Invention

According to the method for producing an organic sulfur compound of the present invention, an organic sulfur compound can be produced safely, efficiently, and by a simple operation.

The compound (β) of the present invention is useful as a crosslinkable monomer.

The carrier of the present invention has excellent pressure resistance, and even when a protein ligand is not immobilized thereon, has a high dynamic binding capacity to a target substance, and has a high performance of separating a target substance from a biological sample.

Therefore, according to the present invention, it is possible to provide a chromatography column which has excellent pressure resistance, and even when a protein ligand is not immobilized thereon, has a high dynamic binding capacity to a target substance, and has a high performance of separating a target substance from a biological sample.

In addition, according to the method for producing a carrier of the present invention, a carrier which has excellent pressure resistance, and even when a protein ligand is not immobilized thereon, has a high dynamic binding capacity to a target substance, and has a high performance of separating a target substance from a biological sample, can be produced safely, efficiently, and by a simple operation.

DESCRIPTION OF EMBODIMENTS

<Method for Producing Organic Sulfur Compound>

The method for producing an organic sulfur compound of the present invention is a method for producing a compound having a divalent group represented by the following Formula (21), the method including reacting a cyclic ether group-containing compound with a thiocarboxylate:

(21)

wherein $R^{51}$ and $R^{52}$ independently represent a divalent group formed by ring-opening a cyclic ether group, $X^2$ represents a thio group, a sulfinyl group, or a sulfonyl group, and

* represents a bond.

(Cyclic Ether Group-Containing Compound)

The method for producing an organic sulfur compound of the present invention uses a cyclic ether group-containing compound.

Here, it is preferred that the "cyclic ether group" in the present specification is a cyclic ether group having 3 to 7 atoms constituting the ring. The cyclic ether group may have an alkyl group as a substituent. Specific examples of the cyclic ether group include cyclic ether groups represented by the following Formulas (3) to (8), but the cyclic ether group represented by Formula (3), (7), or (8) is preferred for improving reaction efficiency, and the cyclic ether group represented by Formula (3) is more preferred:

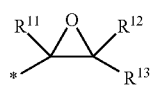

(3)

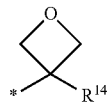

(4)

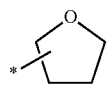

(5)

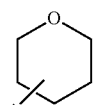

(6)

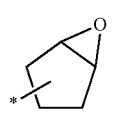

(7)

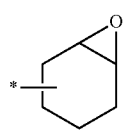

(8)

wherein $R^{11}$ to $R^{14}$ independently represent a hydrogen atom or an alkyl group, and represents a bond.

The alkyl group represented by $R^{11}$ to $R^{14}$ has preferably 1 to 4 carbon atoms, more preferably 1 or 2 carbon atoms. The alkyl group may be linear or branched, and examples thereof include a methyl group, an ethyl group, an n-propyl group, an isopropyl group, an n-butyl group, a sec-butyl group, and a tert-butyl group. Further, $R^{11}$ to $R^{14}$ are preferably a hydrogen atom.

The cyclic ether group-containing compound can be roughly classified into a low molecular weight compound and a high molecular weight compound. Further, the cyclic ether group-containing compound may have a polymerizable functional group other than the cyclic ether group (hereinafter, also referred to as "other polymerizable functional groups"), regardless of whether it is a low molecular weight compound or a high molecular weight compound. That is, the cyclic ether group-containing compound may be a macromonomer.

Further, the cyclic ether group-containing compound may be used alone or in combination of two or more in the reaction. As the cyclic ether group-containing compound, a commercially available product may be used, or a compound prepared with reference to a known method may be used.

—Cyclic Ether Group-Containing Low Molecular Weight Compound—

Here, the cyclic ether group-containing low molecular weight compound will be described in detail.

In the present specification, the "cyclic ether group-containing low molecular weight compound" refers to a cyclic ether group-containing compound other than the "cyclic ether group-containing high molecular weight compound". The cyclic ether group-containing low molecular weight compound has a molecular weight of preferably 40 or more, more preferably 50 or more, particularly preferably 60 or more, and preferably less than 5000, more preferably less than 2500, still more preferably less than 1000, and particularly preferably less than 750. A specific range is preferably 40 or more and less than 5000, more preferably 50 or more and less than 2500, still more preferably 60 or more and less than 1000, and particularly preferably 60 or more and less than 750.

When the cyclic ether group-containing compound is a low molecular weight compound, the number of cyclic ether groups is not particularly limited, but is preferably 1 to 20, more preferably 1 to 6, still more preferably 1 to 4, and particularly preferably 1 or 2 in one molecule. When the number of cyclic ether groups is one, it is easy to obtain a single kind of compound. When the number of cyclic ether groups is 2 or more, for example, a cyclic sulfide compound, a chain sulfide compound, a thio group-containing network polymer, a thio group-containing dendron, a thio group-containing dendrimer, a thio group-containing block copolymer, a thio group-containing star polymer, a thio group-containing ladder polymer, or a thio group-containing hyperbranched polymer can be obtained.

The cyclic ether group-containing low molecular weight compound has a total of preferably 2 to 80, more preferably 2 to 40, still more preferably 3 to 35, even more preferably 3 to 30, and particularly preferably 4 to 25 carbon atoms, for improving solubility and viscosity in a reaction system to increase reaction efficiency.

The cyclic ether group-containing low molecular weight compound can be roughly classified into those having a polymerizable functional group other than the cyclic ether group and those having no other polymerizable functional group. Examples of "other polymerizable functional groups" include a polymerizable unsaturated group.

When the cyclic ether group-containing low molecular weight compound has other polymerizable functional groups, the number of other polymerizable functional groups is preferably 1 to 10, more preferably 1 to 6, still more preferably 1 to 3, and particularly preferably 1 or 2 in one molecule.

Examples of a low molecular weight compounds having one cyclic ether group in the molecule but no other polymerizable functional group include alkylene oxides such as ethylene oxide, propylene oxide, 1,2-butylene oxide, 2,3-butylene oxide, 1,2-epoxypentane, 1,2-epoxyhexane, and 1,2-epoxyheptane (preferably alkylene oxides having 2 to 80 carbon atoms); haloalkylene oxides such as epichlorohydrin, epibromohydrin, and 3-perfluorooctyl-1,2-epoxypropane (preferably haloalkylene oxides having total 2 to 80 carbon atoms); alkyl glycidyl ethers such as glycidyl methyl ether and ethyl glycidyl ether (preferably alkyl glycidyl ethers having total 4 to 80 carbon atoms); hydroxyl group-containing cyclic ether compounds such as glycidol (preferably hydroxyl group-containing cyclic ether compounds having total 2 to 80 carbon atoms); aromatic group-containing cyclic ether compounds such as styrene oxide, benzyl glycidyl ether, and 2-biphenylyl glycidyl ether (preferably aromatic group-containing cyclic ether compounds having total 8 to 80 carbon atoms); silicon-containing cyclic ether compounds such as diethoxy(3-glycidyloxypropyl) methylsilane, 2-(3,4-epoxycyclohexyl)ethyl trimethoxysilane (preferably silicon-containing cyclic ether compounds having total 4 to 80 carbon atoms); and cyclic ether group-containing organic salts such as glycidyltrimethylammonium chloride (preferably cyclic ether group-containing organic salts having 4 to 80 carbon atoms), and these may be used in the reaction alone or in combination of two or more.

Examples of a low molecular weight compound having one cyclic ether group and one other polymerizable functional group each in the molecule include (meth)acrylate-based monomers having a cyclic ether group such as glycidyl (meth)acrylate, 3,4-epoxycyclohexylmethyl (meth)acrylate, 4-hydroxybutyl (meth)acrylate glycidylether, tetrahydrofurfuryl (meth)acrylate, 3-oxiranylpropyl (meth)acrylate, 4-oxiranylbutyl (meth)acrylate, 5-oxiranylpentyl (meth)acrylate, 6-oxiranylhexyl (meth)acrylate, 7-oxiranylheptyl (meth)acrylate, 8-oxiranyloctyl (meth)acrylate, (3-methyloxiranyl)methyl (meth)acrylate, glycerin mono (meth)acrylate glycidylether, 3,4-epoxycyclohexylethyl (meth)acrylate, 3,4-epoxycyclohexylpropyl (meth)acrylate, and α-(meth)acryl-ω-glycidyl polyethyleneglycol (preferably (meth)acrylate-based monomers having a cyclic ether group having total 6 to 80 carbon atoms); aromatic vinyl-based monomers having a cyclic ether group such as vinylbenzyl glycidyl ether (preferably aromatic vinyl-based monomers having a cyclic ether group having total 10 to 80 carbon atoms); allylether-based monomers having a cyclic ether group such as allylglycidyl ether (preferably allylether-based monomers having a cyclic ether group having total 6 to 80 carbon atoms); and vinylalkyleneoxide-based monomers such as 3,4-epoxy-1-butene and alkylene oxide-based monomers having a triple bond such as 2,3-epoxypropyl propargylether, and these may be used in the reaction alone or in combination of two or more.

Examples of a low molecular weight compound having two cyclic ether groups in the molecule but no other polymerizable functional group include diglycidyl ethers such as 1,4-butanediol diglycidyl ether, 1,6-hexanediol diglycidyl ether, bisphenol A diglycidyl ether, ethyleneglycol diglycidyl ether, diethyleneglycol diglycidyl ether, polyethyleneglycol diglycidyl ether, propyleneglycol diglycidyl ether, tripropyleneglycol diglycidyl ether, polypropyleneglycol diglycidyl ether, neopentylglycol diglycidyl ether, and glycerin diglycidyl ether (preferably diglycidyl ethers having total 7 to 80 carbon atoms); diglycidyl dicarboxylates such as diglycidyl 1,2-cyclohexanedicarboxylate, diglycidyl phthalate, and diglycidyl terephthalate (preferably diglycidyl dicarboxylates having total 8 to 80 carbon atoms); diepoxyalkanes such as 1,3-butadiene diepoxide (preferably dipeoxyalkanes having total 4 to 80 carbon atoms); and compounds having two epoxycyclohexyl groups in the molecule such as 1,3-bis[2-(7-oxabicyclo[4.1.0]heptane-3-yl) ethyl]-1,1,3,3-tetramethyldisiloxane (preferably compounds having two epoxycyclohexyl groups in the molecule having total 12 to 80 carbon atoms), these may be used in the reaction alone or in combination of two or more.

Examples of a low molecular weight compound having two cyclic ether groups and one other polymerizable functional group each in the molecule include diglycidyl 4-cyclohexene-1,2-dicarboxylate.

Examples of a low molecular weight compound having two cyclic ether groups and two other polymerizable functional groups each in the molecule include diglycidyl bicyclo[2.2.1]hepta-2,5-diene-2,3-dicarboxylate.

Examples of a low molecular weight compound having three cyclic ether groups in the molecule but no other polymerizable functional group include triglycidyl ethers such as trimethylolpropane triglycidyl ether and glycerol triglycidyl ether (preferably triglycidyl ethers having total 10 to 80 carbon atoms); and triglycidyl isocyanurate, triglycidyl cyanurate, and triglycidyl 1,2,4-benzenetricarboxylate, and these may be used in the reaction alone or in combination of two or more.

Examples of a low molecular weight compound having four cyclic ether groups in the molecule but no other polymerizable functional group include tetraglycidyl ethers such as mathanetetrayl tetrakis (glycidylether), sorbitol tetraglycidyl ether, and pentaerytritol tetraglycidyl ether (preferably tetraglycidylethers having total 13 to 80 carbon atoms), and these may be used in the reaction alone or in combination of two or more.

—Cyclic Ether Group-Containing High Molecular Weight Compound—

Next, the cyclic ether group-containing high molecular weight compound will be described in detail.

In the present specification, the "cyclic ether group-containing high molecular weight compound" refers to, among cyclic ether group-containing compounds, those including a repeated structural unit and having a high molecular weight. The cyclic ether group-containing high molecular weight compound has a weight average molecular weight of preferably 750 or more, more preferably 1000 or more, still more preferably 2500 or more, and particularly preferably 5000 or more, and preferably 2,500,000 or less, more preferably 1,000,000 or less, and particularly preferably 500,000 or less. The weight average molecular weight can be measured by, for example, NMR or GPC.

The cyclic ether group-containing high molecular weight compound may be preferably a high molecular weight compound having a structural unit having a cyclic ether group, and more preferably a high molecular weight compound having a structural unit having a cyclic ether group in a side chain. Further, a monomer which derives a structural unit having a cyclic ether group may be a non-crosslinkable monomer or a crosslinkable monomer.

The monomer which derives a structural unit having a cyclic ether group has a total of preferably 2 to 80, more preferably 2 to 40, still more preferably 3 to 35, even more preferably 3 to 30, and particularly preferably 4 to 25 carbon atoms, for improving solubility and viscosity in a reaction system to increase reaction efficiency.

The monomer which derives a structural unit having a cyclic ether group is preferably those having "other polymerizable functional groups" represented by a polymerizable unsaturated group. The number of other polymerizable functional groups is preferably 1 to 10, more preferably 1 to 6, still more preferably 1 or 2, and particularly preferably one in one molecule of the monomer.

Examples of the monomer which derives a structural unit having a cyclic ether group include a monomer having one cyclic ether group and one other polymerizable functional group each in the molecule, and a monomer having two or more cyclic ether groups in the molecule. Specific examples of such a monomer include, among the compounds listed above as the "cyclic ether group-containing low molecular weight compound", those having one cyclic ether group and one other polymerizable functional group each in the molecule, and those having two or more cyclic ether groups in the molecule. The low molecular weight compound having two or more cyclic ether groups in the molecule may or may not have the above-mentioned "other polymerizable functional groups".

The content of the structural unit having a cyclic ether group is preferably 0.1 to 100% by mass, more preferably 10 to 90° by mass, based on all structural units contained in the high molecular weight compound.

Further, the cyclic ether group-containing high molecular weight compound may have a structural unit other than the structural unit having a cyclic ether group. Examples of the monomer which derives such a structural unit (hereinafter, also referred to as "other monomers MO1") include a polymerizable unsaturated group-containing monomer having no cyclic ether group. Other monomers MO1 are roughly classified into a non-crosslinkable monomer and a crosslinkable monomer, and one of these may be used or used in combination.

The content of the structural unit provided by other monomers MO1 is preferably 0 to 99.9% by mass and more preferably 10 to 90% by mass, based on all structural units contained in the high molecular weight compound.

Examples of the non-crosslinkable monomer include a (meth)acrylate-based non-crosslinkable monomer, a (meth)acrylamide-based non-crosslinkable monomer, an aromatic vinyl-based non-crosslinkable monomer, a vinyl ketone-based non-crosslinkable monomer, a (meth)acrylonitrile-based non-crosslinkable monomer, an N-vinylamide-based non-crosslinkable monomer, and unsaturated dicarbocylate anhydride-based non-crosslinkable monomer. These can be used alone or in combination of two or more. The non-crosslinkable monomer is preferably a (meth)acrylate-based non-crosslinkable monomer and an aromatic vinyl-based non-crosslinkable monomer.

Examples of the (meth)acrylate-based non-crosslinkable monomer include methyl (meth)acrylate, ethyl (meth)acrylate, n-butyl (meth)acrylate, 4-tert-butyl (meth)acrylate, isobutyl (meth)acrylate, n-octyl (meth)acrylate, 2-ethylhexyl (meth)acrylate, cyclohexyl (meth)acrylate, methoxyethyl (meth)acrylate, hydroxyethyl (meth)acrylate, hydroxypropyl (meth)acrylate, glycerol mono(meth)acrylate, trimethylolethane mono(meth)acrylate, trimethylolpropane mono(meth)acrylate, butanetriol mono(meth)acrylate, polyethyleneglycol mono(meth)acrylate, methoxypolyethyleneglycol (meth)acrylate, pentaerythritol mono(meth)acrylate, dipentaerythritol mono(meth)acrylate, and inositolmono(meth)acrylate. These can be used alone or in combination of two or more.

Examples of the (meth)acrylamide-based non-crosslinkable monomer include (meth)acrylamide, dimethyl (meth)acrylamide, hydroxyethyl (meth)acrylamide, (meth)acryloyl morpholine, and diacetone (meth)acrylamide. These can be used alone or in combination of two or more.

Examples of the aromatic vinyl-based non-crosslinkable monomer include styrenes such as styrene, α-methylstyrene, halogenated styrene, 4-methylstyrene, 2,4-dimethylstyrene, 2,4,6-trimethylstyrene, and ethyl vinyl benzene, 4-isopropylstyrene, 4-n-butylstyrene, 4-isobutylstyrene, and 4-tert-butylstyrene; vinyl naphthalenes such as 1-vinylnaphthalene and 2-vinylnaphthalene. These can be used alone or in combination of two or more.

Examples of the vinyl ketone-based non-crosslinkable monomer include ethyl vinyl ketone, propyl vinyl ketone, and isopropyl vinyl ketone. These can be used alone or in combination of two or more.

Examples of the (meth)acrylonitrile-based non-crosslinkable monomer include acrylonitrile and methacrylonitrile. These can be used alone or in combination of two or more.

Examples of the N-vinylamide-based non-crosslinkable monomer include N-vinylacetamide and N-vinylpropionamide. These can be used alone or in combination of two or more.

Examples of the unsaturated dicarboxylic anhydride-based non-crosslinkable monomer include maleic anhydride, methylmaleic anhydride, and glutaconic anhydride. These can be used alone or in combination of two or more.

Examples of the crosslinkable monomer include a (meth)acrylate-based crosslinkable monomer, an aromatic vinyl-based crosslinkable monomer, and an allyl-based crosslinkable monomer. These can be used alone or in combination of two or more. The crosslinkable monomer is preferably a di- to pentafunctional crosslinkable monomer, and more preferably a di- or trifunctional crosslinkable monomer. Among the crosslinkable monomers, a (meth)acrylate-based crosslinkable monomer and an aromatic vinyl-based crosslinkable monomer are preferred.

Examples of the (meth)acrylate-based crosslinkable monomer include ethylene glycol di(meth)acrylate, diethylene glycol di(meth)acrylate, triethylene glycol di(meth)acrylate, tetraethylene glycol di(meth)acrylate, polyethylene glycol di(meth)acrylate, propylene glycol di(meth)acrylate, dipropylene glycol di(meth)acrylate, tripropylene glycol di(meth)acrylate, tetrapropylene glycol di(meth)acrylate, polypropylene glycol di(meth)acrylate, 1,4-butanediol di(meth)acrylate, 1,6-hexanediol di(meth)acrylate, glycerin di(meth)acrylate, trimethylolethane di(meth)acrylate, trimethylolpropane di(meth)acrylate, trimethylolpropane tri(meth)acrylate, butanetriol di(meth)acrylate, pentaerythritol di(meth)acrylate, pentaerythritol tri(meth)acrylate, pentaerythritol tetra(meth)acrylate, glucose di(meth)acrylate, glucose tri(meth)acrylate, glucose tetra(meth)acrylate, dipentaerythritol di(meth)acrylate, dipentaerythritol tri(meth)acrylate, dipentaerythritol tetra(meth)acrylate, dipentaerythritol penta(meth)acrylate, inositol di(meth)acrylate, inositol tri(meth)acrylate, inositol tetra(meth)acrylate, mannitol di(meth)acrylate, mannitol tri(meth)acrylate, mannitol tetra(meth)acrylate, and mannitol penta(meth)acrylate. These can be used alone or in combination of two or more.

Examples of the aromatic vinyl-based crosslinkable monomer include divinylbenzene, trivinylbenzene, divinyltoluene, divinylxylene, divinylethylbenzene, and divinylnaphthalene. Further, the compound represented by Formula (β) of the present invention can also be used as the aromatic vinyl-based crosslinkable monomer. These can be used alone or in combination of two or more.

Examples of the allyl-based crosslinkable monomer include diallyl phthalate, diallyl isophthalate, diallyl terephthalate, diallyl maleate, diallyl fumarate, diallyl itaconate, diallyl trimellitate, triallyl trimellitate, triallyl cyanurate, diallyl isocyanurate, and triallyl isocyanurate. These can be used alone or in combination of two or more.

Further, examples of the crosslinkable monomer include a dehydration condensation reaction product of an amino alcohol such as diaminopropanol, tris(hydroxymethyl)aminomethane, and glucosamine with a (meth)acrylic acid, and a conjugated diolefin such as butadiene and isoprene, in addition to those exemplified above.

The cyclic ether group-containing high molecular weight compound may have a one-dimensional structure or a multi-dimensional structure, and may be any of linear high molecular weight compounds, branched high molecular weight compounds, plate-like high molecular weight compounds, and a network-like high molecular weight compounds. When the cyclic ether group-containing high molecular weight compound is a copolymer, the arrangement of the structural units is arbitrary, and may be any form such as a random copolymer, an alternating copolymer, a block copolymer, and a graft copolymer.

Further, a carrier used for, for example, various purifications such as affinity purification or detection or in vitro diagnosis of bio-related substances, or a support thereof can also be used in a reaction of introducing a thio group as the cyclic ether group-containing high molecular weight compound. Examples of the form of the carrier and the support include particles, monoliths, films, and chips. The carrier and its support may be a commercially available product, or one prepared with reference to a known method described in, for example, WO 2015/119255 A.

(Thiocarboxylate)

A method for producing an organic sulfur compound of the present invention is to react a thiocarboxylate with a cyclic ether group-containing compound. Thus, a reaction of ring-opening two cyclic ether groups and introducing a thio group therebetween can proceed safely and efficiently.

The thiocarboxylate may also be present as an ion in a reaction system. Further, it is also included in "reacting the cyclic ether group-containing compound with the thiocarboxylate" in the present invention to create a state in which the thiocarboxylate and its ion are present in the reaction system by, for example, adding a basic substance to the reaction system with the thiocarboxylic acid.

Examples of the thiocarboxylic acid salt include alkali metal salts such as sodium salts, potassium salts, and lithium salts; salts with Group 2 elements such as calcium salts and magnesium salts; and ammonium salts, pyridinium salts, imidazolium salts, morpholinium salts, pyperidinium salts, pyrrolidinium salts, phosphonium salts, and sulfonium salts. Among these, alkali metal salts are preferred, for efficiently obtaining a desired compound.

As the thiocarboxylate, those represented by the following Formula (13) are preferred, for efficiently obtaining a desired compound.

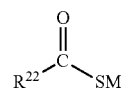

(13)

wherein

R²² represents a hydrogen atom or a monovalent organic group, and

M represents a cation which forms the thiocarboxylate.

In Formula (13), $R^{22}$ represents a hydrogen atom or a monovalent organic group, but a monovalent organic group is preferred, for efficiently obtaining a desired compound. Examples of the monovalent organic group include a substituted or unsubstituted hydrocarbon group. The hydrocarbon group in $R^{22}$ has a concept including an aliphatic hydrocarbon group, an alicyclic hydrocarbon group, and an aromatic hydrocarbon group. Among these, an aliphatic hydrocarbon group and an aromatic hydrocarbon group are preferred, and an aliphatic hydrocarbon group is more preferred, for efficiently obtaining a desired compound.

The aliphatic hydrocarbon group has preferably 1 to 20, more preferably 1 to 12, still more preferably 1 to 6, and particularly preferably 1 to 3 carbon atoms, for efficiently obtaining a desired compound. The aliphatic hydrocarbon group may be linear or branched. The aliphatic hydrocarbon group may be an alkyl group, for efficiently obtaining a desired compound. Examples of the alkyl group include a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl groups, and a dodecyl group.

The alicyclic hydrocarbon group has preferably 3 to 12, and more preferably 3 to 8 carbon atoms, for efficiently obtaining a desired compound. Specific examples of the alicyclic hydrocarbon group include cycloalkyl groups such as a cyclopropyl group, a cyclobutyl group, a cyclopentyl group, and a cyclohexyl group.

The aromatic hydrocarbon group has preferably 6 to 12, and more preferably 6 to 8 carbon atoms, for efficiently obtaining a desired compound. Specific examples of the aromatic hydrocarbon group include aryl groups such as a phenyl group, a tolyl group, a xylyl group, and a naphthyl group.

Examples of the substituent in $R^{22}$ include halogen atoms such as a fluorine atom, a chlorine atom, a bromine atom, and an iodine atom.

In addition, M represents a cation forming a thiocarboxylate. Examples of M include alkali metal ions such as a sodium ion, a potassium ion, and a lithium ion; Group 2 element ions such as a calcium ion and a magnesium ion; and an ammonium ion, a pyridinium ion, an imidazolium ion, a morpholinium ion, a piperidinium ion, a pyrrolidinium ion, a phosphonium ion, and a sulfonium ion. Among these, alkali metal ions are preferred, for efficiently obtaining a desired compound.

Specific examples of the thiocarboxylate include thioformate, thioacetate, propanethioate, butanethioate, pentanethioate, hexanethioate, octanethioate, nonanethioate, decanethioate, dodecanethioate, and thiobenzoate. Among these, a thioacetate is preferred, and an alkali metal salt of a thioacetic acid is particularly preferred, for efficiently obtaining a desired compound.

Further, the thiocarboxylate may be used alone or in combination of two or more in the reaction. As the thiocarboxylate, a commercially available product may be used, or a compound prepared with reference to a known method may be used.

The amount of the thiocarboxylate used is preferably 0.01 mol or more, more preferably 0.05 mol or more, still more preferably 0.1 mol or more, still more preferably 0.25 mol or more, and particularly preferably 0.5 mol or more, with respect to 1 mol of the cyclic ether group, for efficiently obtaining a desired compound, and preferably 5 mol or less, more preferably 2.5 mol or less, still more preferably 1 mol or less, and particularly preferably 0.75 mol or less, with respect to 1 mol of the cyclic ether group, for efficiently obtaining a desired compound. When the amount of the thiocarboxylate used is 0.75 mol or less with respect to 1 mol of the cyclic ether group, the desired compound can be obtained particularly efficiently. As a specific range, 0.01 mol or more and 5 mol or less is preferred, 0.05 mol or more and 2.5 mol or less is more preferred, 0.1 mol or more and 1 mol or less is still more preferred, and 0.25 mol or more and 0.75 mol or less is particularly preferred.

(Reaction Conditions and Others)

The reaction of the cyclic ether group-containing compound with the thiocarboxylate (reaction of introducing a thio group) can be carried out in the presence or absence of a solvent, but it is preferred to carry out the reaction in the presence of a solvent, for efficiently obtaining a desired compound.

Solvents include water; alcohols such as methanol, ethanol, propanol, isopropyl alcohol, and n-butyl alcohol; sulfoxides such as dimethyl sulfoxide; ketones such as acetone and methyl ethyl ketone; ethers such as diethyl ether and tetrahydrofuran; esters such as ethyl acetate and butyl acetate; amides such as N, N-dimethylformamide; and nitriles such as acetonitrile, and these may be used alone or in combination of two or more. As the solvent, a hydrous solvent (water or a mixed solution of water and a solvent other than water) is preferred, for efficiently obtaining a desired compound. The content of water in the hydrous solvent is preferably 3 to 100% by mass, more preferably 20 to 100% by mass, for efficiently obtaining a desired compound.

Among these solvents, one or more solvents selected from water, alcohols, sulfoxides, ketones, ethers and amides are preferred, and one or more solvents selected from water, alcohols, and sulfoxides are particularly preferred, for efficiently obtaining a desired compound.

The amount of the solvent used is usually 0 to 10000 parts by mass, preferably 10 to 2000 parts by mass, with respect to 100 parts by mass of the cyclic ether group-containing compound.

Further, the reaction of introducing a thio group may be carried out using a basic catalyst such as N,N-diisopropylethylamine, but it is also possible to proceed with the reaction without using a catalyst.

Examples of the reaction conditions for the reaction of introducing a thio group include a basic condition, a neutral condition, and an acidic condition, but it is preferred to carry out the reaction of introducing a thio group under a neutral to basic condition, for efficiently obtaining a desired compound. The pH of the reaction of introducing a thio group is preferably 6 or more, more preferably 6 to 14, and particularly preferably 7 to 14, for efficiently obtaining a desired compound.

Here, the "neutral to basic condition" described above means that a neutral to basic state is created in the reaction system when the cyclic ether group-containing compound reacts with the thiocarboxylate, and whether a component other than the cyclic ether group-containing compound and the thiocarboxylate (such as a basic substance) is added or not, in the case in which a neutral to basic state is created in the reaction system, it corresponds to a reaction under the "neutral to basic condition" That is, examples of the case "under the neutral to basic condition" include the case in which the inside of the system spontaneously becomes basic by the reaction of the cyclic ether group-containing compound with the thiocarboxylate, the case in which a basic substance is attached to make the inside of the reaction system in a range of neutral to basic, and the case in which a state in which a thiocarboxylate and its ion are present in the reaction system by, for example, adding a thiocarboxylic acid to the reaction system with a basic substance instead of the thiocarboxylate is created to make the inside of the reaction system in a range of neutral to basic.

The same applies to pH described above, and for example, "pH 6 or higher" means that a state of pH 6 or higher is created in the reaction system when the cyclic ether group-containing compound reacts with the thiocarboxylate, and whether a component other than the cyclic ether group-containing compound and the thiocarboxylate (such as a basic substance) is added or not, in the case in which a pH 6 or higher state is created in the reaction system, it corresponds to a reaction under "pH 6 or higher".

The reaction temperature of the reaction of introducing a thio group is usually 0 to 120° C., preferably 20 to 80° C.

The reaction time of the reaction of introducing a thio group is usually 0.01 to 24 hours, preferably 0.5 to 8 hours.

The reaction pressure of the reaction of introducing a thio group is not particularly limited, and the reaction can be carried out at normal pressure.

According to the reaction of introducing a thio group, a wide variety of sulfide compounds (compounds in which $X^2$ is a thio group in Formula (21)) can be obtained depending on the kind of the cyclic ether group-containing compound. For example, a cyclic ether group-containing compound and a cyclic ether group-containing compound of a molecule different from the compound (these cyclic ether group-containing compounds may be the same kind or different kinds) can be ring-opened, respectively to introduce a thio group therebetween and be connected, or two cyclic ether groups included in one molecule can be ring-opened to introduce a thio group therebetween to introduce a cross-linked structure in the molecule.

More specifically, when a low molecular weight compound having one cyclic ether group and one other polymerizable functional group each in the molecule (for example, glycidyl (meth)acrylate and vinylbenzyl glycidyl ether) is used as the cyclic ether group-containing compound, a sulfide compound having other polymerizable functional groups can be obtained.

When a low molecular weight compound having two cyclic ether groups in the molecule (for example, 1,4-butanediol diglycidyl ether, bisphenol A diglycidyl ether, and ethylene glycol diglycidyl ether) is used as the cyclic ether group-containing compound, a cyclic sulfide compound or a chain sulfide compound can be obtained.

When a low molecular weight compound having three or more cyclic ether groups (for example, triglycidyl isocyanurate) is used as the cyclic ether group-containing compound, a thio group-containing network polymer can be obtained.

When a high molecular weight compound having two or more cyclic ether groups is used as the cyclic ether group-containing compound, a high molecular weight compound having a crosslinked structure containing a divalent group represented by Formula (21) can be obtained.

Then, the sulfide compound obtained as described above may be isolated by appropriately combining usual means such as filtration, washing, drying, recrystallization, reprecipitation, dialysis, centrifugation, extraction with various solvents, neutralization, and chromatography as needed.

When a compound in which $X^2$ is a sulfinyl group or a sulfonyl group in Formula (21) is produced, a compound in which $X^2$ is a thio group in Formula (21), obtained in the reaction of introducing a thio group (sulfide compound) may be oxidized.

The oxidation may be carried out with reference to known methods described in for example, WO 2015/119255 A and JP 2016-50897 A, and specific examples thereof include a method using an oxidizing agent. Examples of the oxidizing agent include organic oxidizing agents such as peracetic acid, perbenzoic acid, metachloroperbenzoic acid, and tert-butyl hydroperoxide; and inorganic oxidizing agents such as hydrogen peroxide, chromic acid, and permanganate. These oxidizing agents can be used alone or in combination of two or more.

When, for example, a high molecular weight compound having a structural unit having a cyclic ether group is used in the reaction of introducing a thio group as the cyclic ether group-containing compound, the cyclic ether group may remain in the product of the reaction of introducing a thio group, but the remaining cyclic ether group may be ring-opened by a known method. Specific examples of the method include a method for reacting a mercapto group-containing alcohol such as mercaptoethanol or thioglycerol or a polyhydric alcohol such as glycerol with a cyclic ether group.

When the product of the reaction of introducing a thio group has other polymerizable functional groups, the product can be polymerized. At this time, it may be copolymerized with other monomers MO1.

When the compound containing a divalent group represented by the following Formula (21), obtained by the method for producing an organic sulfur compound of the present invention, is a low molecular weight compound, it is useful as, for example, an organic solvent, a surfactant, a hydrophilizing agent, a dispersion stabilizer, and a cross-linking agent. When the compound is a high molecular weight compound, it is useful as, for example, a carrier used for, for example, various purifications such as affinity purification or detection or in vitro diagnosis of bio-related substances, or a support thereof, a dispersion stabilizer, a gelling agent, and a curing agent.

(21)

wherein $R^{51}$ and $R^{52}$ independently represent a divalent group formed by ring-opening a cyclic ether group, $X^2$ represents a thio group, a sulfinyl group, or a sulfonyl group, and

* represents a bond.

The divalent group formed by ring-opening the cyclic ether group represented by $R^{51}$ and $R^{52}$ corresponds to the cyclic ether group contained in the cyclic ether group-containing compound, and for example, is a ring-opening epoxy group as shown by —CHOH—CH$_2$—, when the cyclic ether group contained in the cyclic ether group-containing compound is an epoxy group.

Further, among the compounds containing a divalent group represented by Formula (21) obtained by the method for producing an organic sulfur compound of the present invention, the compound represented by the following Formula (β) is a novel compound. Since the compound (β) has a plurality of polymerizable unsaturated groups, it is useful as a crosslinkable monomer, and for example, can be used as a raw material monomer of a carrier used for, for example, various purifications such as affinity purification or detection or in vitro diagnosis of bio-related substances. Further, it has characteristics such as higher structural flexibility and hydrophilicity than divinylbenzene which is a crosslinkable monomer, and is particularly useful as an alternative monomer such as divinylbenzene.

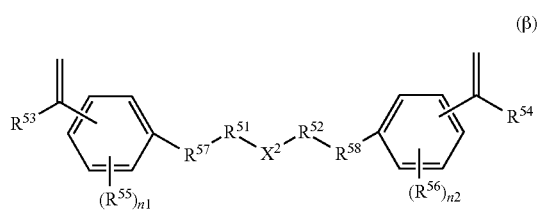

(β)

wherein $R^{51}$ and $R^{52}$ independently represent a divalent group formed by ring-opening of a cyclic ether group, $R^{53}$ and $R^{54}$ independently represent a hydrogen atom or a methyl group, $R^{55}$ and $R^{56}$ independently represent a halogen atom or an organic group, $R^{57}$ and $R^{58}$ independently represent a single bond or a divalent linking group, $X^2$ represents a thio group, a sulfinyl group, or a sulfonyl group, and n1 and n2 independently represent an integer from 0 to 4.

In Formula (β), $R^{51}$ and $R^{52}$ independently represent a divalent group formed by ring-opening the cyclic ether group, but $R^{51}$ and $R^{52}$ are equivalent to $R^{51}$ and $R^{52}$ in Formula (21).

$R^{55}$ and $R^{56}$ independently represent a halogen atom or an organic group.

Examples of the halogen atom represented by $R^{55}$ and $R^{56}$ include a fluorine atom, a chlorine atom, a bromine atom, and an iodine atom.

Examples of the organic group represented by $R^{55}$ and $R^{56}$ include a substituted or unsubstituted hydrocarbon group and a group in which the carbon atoms of the substituted or unsubstituted hydrocarbon group are partially replaced with one or more selected from an ether bond, an amide bond, and an ester bond, but the substituted or unsubstituted hydrocarbon group is preferred. In addition, in the group in which the carbon atoms of the substituted or unsubstituted hydrocarbon group are partially replaced with one or more selected from an ether bond, an amide bond, and an ester bond, the number of ether bonds, amide bonds, and ester bonds may be one or two or more.

The organic group represented by $R^{55}$ and $R^{56}$ has a total of preferably 1 to 20, more preferably 1 to 10, still more preferably 1 to 6, and particularly preferably 1 to 3 carbon atoms.

The "hydrocarbon group" in $R^{55}$ and $R^{56}$ may or may not have a substituent. Examples of the substituted or unsubstituted hydrocarbon group include the same as the substituted or unsubstituted hydrocarbon group represented by $R^{22}$ in Formula (13). When n1 is an integer of 2 to 4, n1 $R^{55}$s may be the same or different, and when n2 is an integer of 2 to 4, n2 $R^{56}$s may be the same or different.

n1 and n2 independently represent an integer of 0 to 4, preferably 0 or 1, and more preferably 0.

$R^{57}$ and $R^{58}$ independently represent a single bond or a divalent linking group, but a divalent linking group is preferred, and a divalent organic group is more preferred.

The divalent organic group represented by $R^{57}$ and $R^{58}$ is preferably a substituted or unsubstituted divalent hydrocarbon group and a group in which the carbon atoms of the substituted or unsubstituted divalent hydrocarbon group are partially replaced with one or more selected from an ether bond, an amide bond, and an ester bond, and more preferably a substituted or unsubstituted divalent hydrocarbon group and a group in which the carbon atoms of the substituted or unsubstituted divalent hydrocarbon group are partially replaced with an ether bond.

In addition, in the group in which the carbon atoms of the substituted or unsubstituted divalent hydrocarbon group are partially replaced with one or more selected from an ether bond, an amide bond, and an ester bond, the number of ether bonds, amide bonds, and ester bonds may be one or two or more.

The divalent organic group has a total of preferably 1 to 20, more preferably 1 to 10, still more preferably 1 to 6, and particularly preferably 1 to 3 carbon atoms.

The "divalent hydrocarbon group" in $R^{57}$ and $R^{58}$ is preferably any one of a divalent aliphatic hydrocarbon group, a divalent alicyclic hydrocarbon group, and a divalent aromatic hydrocarbon group, but a divalent aliphatic hydrocarbon group is preferred.

The divalent aliphatic hydrocarbon group has preferably 1 to 20, more preferably 1 to 10, still more preferably 1 to 6, and particularly preferably 1 to 3 carbon atoms. The divalent aliphatic hydrocarbon group may be linear or branched. The divalent aliphatic hydrocarbon group is preferably an alkanediyl group. Examples of the alkanediyl group include a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,4-diyl group, a pentane-1,5-diyl group, and a hexane-1,6-diyl group.

The group in which the carbon atoms of the substituted or unsubstituted divalent hydrocarbon group are partially replaced with an ether bond is preferably a group represented by —$(R^gO)_{q2}R^h$—.

Here, $R^g$ and $R^h$ independently represent a divalent hydrocarbon group having 1 to 8 carbon atoms (preferably 1 to 4 carbon atoms, more preferably 1 or 2 carbon atoms), and q2 represents an integer of 1 to 6 (preferably an integer of 1 to 3, more preferably 1 or 2). Examples of the alkanediyl group represented by $R^g$ and $R^h$ include the same as exemplified in $R^{57}$ and $R^{58}$. When q2 is an integer of 2 to 6, q2 $R^g$s may be the same or different.

Specific examples of the group represented by —$(R^gO)_{q2}R^h$— include —$CH_2$—O—$CH_2$—, —$CH_2$—O—$CH_2$—O—$CH_2$—, —$CH_2CH_2$—O—$CH_2CH_2$—, and —$CH_2CH_2$—O—$CH_2CH_2$—O—$CH_2CH_2$—.

Examples of the substituent in $R^{57}$ and $R^{58}$ include halogen atoms such as a fluorine atom, a chlorine atom, a bromine atom, and an iodine atom.

<Carrier>

The carrier of the present invention includes a polymer having a crosslinked structure containing a divalent group represented by the following Formula (1) (hereinafter, also referred to as "divalent group (1)"):

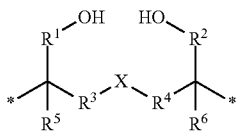

(1)

wherein
$R^1$ to $R^4$ independently represent a single bond or a divalent hydrocarbon group,
$R^5$ and $R^6$ independently represent a hydrogen atom or a hydrocarbon group,
X represents a thio group, a sulfinyl group, a sulfonyl group, an oxy group, >N(—$R^{31}$), >Si(—$R^{32}$)$_2$, >P(—$R^{33}$) >P(=O)(—$R^{34}$), >B(—$R^{35}$), or >C(—$R^{36}$)$_2$ ($R^{31}$ to $R^{36}$ independently represent a hydrogen atom or hydrocarbon group), and
* represents a bond,
with a proviso that when both $R^1$ and $R^3$ are a divalent hydrocarbon group, $R^1$ and $R^3$ may form a ring together with an adjacent carbon atom, and
when both $R^2$ and $R^4$ are a divalent hydrocarbon group, $R^2$ and $R^4$ may form a ring together with an adjacent carbon atom.

(Specific Crosslinked Structure)

The specific crosslinked structure contains the divalent group (1).

In Formula (1), $R^1$ to $R^4$ independently represent a single bond or a divalent hydrocarbon group.

The divalent hydrocarbon group represented by $R^1$ to $R^4$ has preferably 1 to 20, more preferably 1 to 10, still more preferably 1 to 4, and particularly preferably 1 or 2 carbon atoms, for improving pressure resistance, a dynamic binding capacity to a target substance, and a performance of separating a target substance.

The divalent hydrocarbon group represented by $R^1$ to $R^4$ may be a divalent saturated hydrocarbon group or a divalent unsaturated hydrocarbon group. Examples of the divalent hydrocarbon group include a divalent aliphatic hydrocarbon group, a divalent alicyclic hydrocarbon group, and a divalent aromatic hydrocarbon group, but a divalent aliphatic hydrocarbon group is preferred for improving pressure resistance, a dynamic binding capacity to a target substance, and a performance of separating a target substance. The divalent aliphatic hydrocarbon group may be linear or branched.

When the divalent hydrocarbon group represented by $R^1$ to $R^4$ is the divalent aliphatic hydrocarbon group, it has preferably 1 to 20, more preferably 1 to 10, still more preferably 1 to 4, and particularly preferably 1 or 2 carbon atoms, for improving pressure resistance, a dynamic binding capacity to a target substance, and a performance of separating a target substance. Examples of the divalent aliphatic hydrocarbon group include an alkanediyl group and an alkenediyl group, but an alkanediyl group is preferred for improving pressure resistance, a dynamic binding capacity to a target substance, and a performance of separating a target substance.

Specific examples of the alkanediyl group include a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,1-diyl group, a butane-1,2-diyl group, a butane-1,3-diyl group, a butane-1,4-diyl group, a pentane-1,4-diyl group, a pentane-1,5-diyl group, a hexane-1,2-diyl group, a hexane-1,5-diyl group, a hexane-1,6-diyl group, a heptane-1,7-diyl group, an octane-1,8-diyl group, a nonane-1,9-diyl group, a decane-1,2-diyl group, and a decane-1,10-diyl group.

When the divalent hydrocarbon group represented by $R^1$ to $R^4$ is the divalent alicyclic hydrocarbon group, it has preferably 3 to 20, more preferably 3 to 14, still more preferably 3 to 10, and particularly preferably 3 to 8 carbon atoms. Examples of the divalent alicyclic hydrocarbon group include cycloalkanediyl groups such as a cyclohexanediyl group, a methylcyclohexanediyl group, and a cycloheptanediyl group, and a divalent bridged ring hydrocarbon group such as an adamantylene group.

When the divalent hydrocarbon group represented by $R^1$ to $R^4$ is the divalent aromatic hydrocarbon group, it has preferably 6 to 18, and more preferably 6 to 12 carbon atoms. The divalent aromatic hydrocarbon group is preferably an arylene group, and specific examples thereof include a phenylene group and a naphthylene group.

A bonding site of the divalent alicyclic hydrocarbon group and A bonding site of the divalent aromatic hydrocarbon group may be on any carbon on the ring.

Examples of a ring in which $R^1$ and $R^3$, and $R^2$ and $R^4$ may be formed together, respectively include cycloalkane rings having total 3 to 10 carbon atoms (preferably total 5 to 7 carbon atoms), such as a cyclopentane ring, a cyclohexane ring, a methylcyclohexane ring, a cycloheptane ring, and a cyclooctane ring. Among these, a cyclopentane ring and a cyclohexane ring are preferred. The site in which a hydroxyl group and X are bonded in Formula (1) may be on any carbon on the ring.

The divalent hydrocarbon group represented by $R^1$ to $R^4$ may or may not have a substituent. Examples of the substituent include halogen atoms such as a chlorine atom, a bromine atom, and a fluorine atom, and a hydroxyl group. The substitution position and the number of substituents are arbitrary, and when two or more substituents are present, the substituents may be the same or different.

As combinations of $R^1$ to $R^4$,
a combination in which $R^1$ and $R^2$ are a single bond and $R^3$ and $R^4$ independently are a divalent hydrocarbon group,
a combination in which $R^1$ is a single bond, $R^2$, $R^3$, and $R^4$ independently are a divalent hydrocarbon group, and $R^2$ and $R^4$ are combined with an adjacent carbon atom to form a ring,
a combination in which $R^2$ is a single bond, $R^1$, $R^3$, and $R^4$ independently are a divalent hydrocarbon group, and $R^1$ and $R^3$ are combined with an adjacent carbon atom to form a ring, and
a combination in which $R^1$ to $R^4$ independently are a divalent hydrocarbon group, $R^1$ and $R^3$ are combined with an adjacent carbon atom to form a ring, and $R^2$ and $R^4$ are combined with an adjacent carbon atom to form a ring are preferred,
a combination in which $R^1$ and $R^2$ are a single bond, and $R^3$ and $R^4$ independently are a divalent hydrocarbon group, and
a combination in which $R^1$ to $R^4$ independently are a divalent hydrocarbon group, $R^1$ and $R^3$ are combined with an adjacent carbon atom to form a ring, and $R^2$ and $R^4$ are combined with an adjacent carbon atom to form a ring are more preferred,
a combination in which $R^1$ and $R^2$ are a single bond, and $R^3$ and $R^4$ independently are a divalent hydrocarbon group is still more preferred, a combination in which $R^1$ and $R^2$ is a single bond and $R^3$ and $R^4$ independently are a divalent hydrocarbon group having 1 to 10 carbon atoms is still more preferred, and a combination in which $R^1$ and $R^2$ is a single bond and $R^3$ and $R^4$ independently are an alkanediol group having 1 to 4 carbon atoms is still more preferred, for improving pressure resistance, a dynamic binding capacity to a target substance, and a performance of separating a target substance.

$R^5$ and $R^6$ independently represent a hydrogen atom or a hydrocarbon group. Among these, a hydrogen atom is preferred, for improving pressure resistance, a dynamic binding capacity to a target substance, and a performance of separating a target substance.

The hydrocarbon group represented by $R^5$ and $R^6$ is a concept including an aliphatic hydrocarbon group, an alicyclic hydrocarbon group, and an aromatic hydrocarbon group, and may be a saturated hydrocarbon group or an unsaturated hydrocarbon group. The hydrocarbon group has preferably 1 to 4 carbon atoms, more preferably 1 or 2 carbon atoms. The hydrocarbon group is preferably an aliphatic hydrocarbon group, more preferably an alkyl group. The alkyl group may be linear or branched, and examples thereof include a methyl group, an ethyl group, an n-propyl group, an isopropyl group, an n-butyl group, a sec-butyl group, and a tert-butyl group.

X represents a thio group, a sulfinyl group, a sulfonyl group, an oxy group, $>N(-R^{31})$, $>Si(-R^{32})_2$, $>P(-R^{33})$, $>P(=O)(-R^{34})$, $>B(-R^{35})$, or $>C(-R^{36})_2$, but is preferably a thio group, a sulfinyl group, or a sulfonyl group, and is particularly preferably a thio group.

$R^{31}$ to $R^{36}$ independently represent a hydrogen atom or a hydrocarbon group. Examples of the hydrocarbon group represented by $R^{31}$ to $R^{36}$ include the same as the hydrocarbon group represented by $R^5$.

The specific crosslinked structure is not particularly limited as long as it contains the divalent group (1) and may be a divalent crosslinked structure or a trivalent or higher crosslinked structure, but preferably a di- to hexavalent crosslinked structure, more preferably di- and trivalent crosslinked structure, and particularly preferably a divalent crosslinked structure, for improving pressure resistance, a dynamic binding capacity to a target substance, and a performance of separating a target substance.

The number of divalent groups represented by Formula (1) is preferably 1 to 9, more preferably 1 to 5, and particularly preferably 2 or 3 in one specific crosslinked structure, for improving pressure resistance, a dynamic binding capacity to a target substance, and a performance of separating a target substance.

The specific crosslinked structure has a total of preferably 2 or more, more preferably 3 or more, still more preferably 4 or more, still more preferably 5 or more, and particularly preferably 6 or more, and preferably 60 or less, more preferably 40 or less, still more preferably 30 or less, still more preferably 20 or less, and particularly preferably 18 or less carbon atoms, for improving pressure resistance, a dynamic binding capacity to a target substance, and a performance of separating a target substance.

Specific examples of the specific crosslinked structure include a crosslinked structure represented by the following Formula (2):

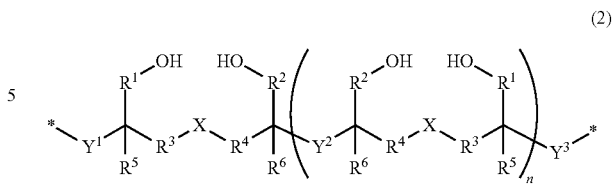

(2)

wherein $Y^1$, $Y^2$, and $Y^3$ independently represent a single bond or a divalent linking group, n represents an integer or 0 or more, and other symbols are as defined above.

In Formula (2), n represents an integer of 0 or more, but is preferably 0 to 8, more preferably 0 to 4, and particularly preferably 1 or 2, for improving pressure resistance, a dynamic binding capacity to a target substance, and a performance of separating a target substance. When n is an integer of 2 or more, n $Y^2$s may be the same or different. Further, when n is an integer of 1 or more, n+1 Xs in Formula (2) may be the same or different. The same applies to $R^1$ to $R^6$.

In Formula (2), examples of the divalent linking group represented by $Y^1$ to $Y^3$ include an alkanediyl group, a group having an ether bond, a thio group, a sulfinyl group, or a sulfonyl group between carbon-carbon atoms of an alkanediyl group having 2 or more carbon atoms, an arylene group, $-C(=O)O-R^7-$, $-C(=O)NH-R^8-$, $-Ar-R^9-**$, or $-Ar-OR^{10}-$.

Here, Ar represents an arylene group.  in $Y^1$ and $Y^3$ may be a bond bonded to the carbon atom in Formula (2) or a bond to the other end, but a bond bonded to the carbon atom in Formula (2) is preferred. Note that  in $Y^2$ may be bonded to either of the carbon atoms adjacent to $R^2$ in Formula (2). Examples of the arylene group represented by $Y^1$ to $Y^3$ and Ar include a phenylene group, a naphthylene group, and a phenanthrenylene group.

$R^7$ to $R^{10}$ independently represent an alkanediyl group or a group having an ether bond, a thio group, a sulfinyl group, or a sulfonyl group between carbon-carbon atoms of an alkanediyl group having 2 or more carbon atoms.

The alkanediyl group represented by $Y^1$ to $Y^3$ and $R^7$ to $R^{10}$ has preferably 1 to 12, more preferably 1 to 6, and particularly preferably 1 to 3 carbon atoms. The alkanediyl group may be linear or branched. Specific examples of the alkanediyl group include a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,1-diyl group, a butane-1,2-diyl group, a butane-1,3-diyl group, a butane-1,4-diyl group, a pentane-1,1-diyl group, a pentane-1,2-diyl group, a pentane-1,3-diyl group, a pentane-1,4-diyl group, a pentane-1,5-diyl group, a hexane-1,1-diyl group, a hexane-1,2-diyl group, a hexane-1,3-diyl group, a hexane-1,4-diyl group, a hexane-1,5-diyl group, a hexane-1,6-diyl group, a heptane-1,7-diyl group, and an octane-1,8-diyl group.

The "group having an ether bond, a thio group, a sulfinyl group, or a sulfonyl group between carbon-carbon atoms of an alkanediyl group having 2 or more carbon atoms" represented by $Y^1$ to $Y^3$ and $R^7$ to $R^{10}$ is preferably a group represented by $-R^a(X^aR^b)_tX^bR^c-$ ($R^a$, $R^b$, and $R^c$ independently represent an alkanediyl group having 1 to 4 carbon atoms, $X^a$ and $X^b$ independently represent an ether bond, a thio group, a sulfinyl, or a sulfonyl group, and t represents an integer of 0 to 30).

The alkanediyl group represented by $R^a$, $R^b$, and $R^c$ may be linear or branched. Specific examples thereof include a methane-1,1-diyl group, an ethane-1,1-diyl group, an ethane-1,2-diyl group, a propane-1,1-diyl group, a propane-1,2-diyl group, a propane-1,3-diyl group, a propane-2,2-diyl group, a butane-1,1-diyl group, a butane-1,2-diyl group, a butane-1,3-diyl group, and a butane-1,4-diyl group. t is preferably an integer of 0 to 20, more preferably an integer of 0 to 10, still more preferably an integer of 0 to 5, and particularly preferably 0. When t is an integer of 2 to 30, t $R^b$s may be the same or different. The same applies to $X^a$.

Preferable specific examples of the group having an ether bond, a thio group, a sulfinyl group, or a sulfonyl group between carbon-carbon atoms of an alkanediyl group having 2 or more carbon atoms include a group represented by —$R^a X^b R^c$—.

The alkanediyl group represented by $Y^1$ to $Y^3$ and $R^7$ to $R^{10}$ and the group having an ether bond, a thio group, a sulfinyl group, or a sulfonyl group between carbon-carbon atoms of an alkanediyl group having 2 or more carbon atoms may or may not have a substituent. Examples of the substituent include a hydroxyl group.

When $Y^1$ and $Y^3$ are a divalent linking group, the divalent linking group is particularly preferably —C(=O)O—$R^7$—**.

$Y^2$ is preferably a single bond or a group having an ether bond, a thio group, a sulfinyl group, or a sulfonyl group between carbon-carbon atoms of an alkanediyl group having 2 or more carbon atoms, more preferably a single bond or a group having a thio group, a sulfinyl group, or a sulfonyl group between carbon-carbon atoms of an alkanediyl group having 2 or more carbon atoms, and particularly preferably a single bond, for improving pressure resistance, a dynamic binding capacity to a target substance, and a performance of separating a target substance.

The content of the specific crosslinked structure is preferably 0.1 to 90% by mass, more preferably 1 to 60% by mass, and particularly preferably 3 to 50% by mass, with respect to the total amount of the polymer, for improving pressure resistance, a dynamic binding capacity to a target substance, and a performance of separating a target substance.

The content of each structure in the polymer can be measured by, for example, elemental analysis or pyrolysis gas chromatography.

(Polymer)

The polymer included in the carrier of the present invention is not particularly limited as long as it has a specific crosslinked structure in the molecule, and may be a synthetic polymer or a natural polymer, but is preferably a synthetic polymer. The polymer is preferably a water-insoluble polymer.

Examples of the synthetic polymer include polymers having one or two or more selected from a (meth)acrylate-based monomer-derived structural unit, a (meth)acrylamide-based monomer-derived structural unit, a (meth)acrylonitrile-based monomer-derived structural unit, an aromatic vinyl-based monomer-derived structural unit, a vinylether-based monomer-derived structural unit, a vinylketone-based monomer-derived structural unit, an N-vinylamide-based monomer-derived structural unit, a vinylalkyleneoxide-based monomer-derived structural unit, an alkyleneoxide-based monomer-derived structural unit having a triple bond, an allyl-based monomer-derived structural unit, an unsaturated dicarboxylic anhydride-based monomer-derived structural unit, an epoxy-based monomer-derived structural unit, and an unsaturated polyalkyleneglycolether-based monomer-derived structural unit. Examples of the natural polymer include those formed of polysaccharides such as agarose, cellulose (such as crystalline cellulose), and dextran.

The content of the polymer in the carrier of the present invention is preferably 80 to 100% by mass, more preferably 90 to 100% by mass, and particularly preferably 99 to 100% by mass.

The polymer included in the carrier of the present invention may have a reactive functional group σ in the molecule, in addition to the specific crosslinked structure.

The reactive functional group σ is preferably those which can react with a sulfanyl group or a thiocarboxylate, or those which can react with an antibody. Examples thereof include one or more functional groups selected from the group consisting of a cyclic ether group, a carboxyl group, —C(=O)—O—C(=O)—, an N-succinimidyl group, a formyl group, an isocyanate group, a maleimide group, and a haloacetyl group (such as an iodoacetyl group or bromoacetyl group). Among these, a cyclic ether group and an N-succinimidyl group are preferred, and a cyclic ether group is particularly preferred, for improving pressure resistance, a dynamic binding capacity to a target substance, and a performance of separating a target substance. The "cyclic ether group" is the same as the "cyclic ether group" contained in the cyclic ether group-containing compound used in the method for producing an organic sulfur compound of the present invention. The cyclic ether group is preferably a cyclic ether group represented by Formula (3), for improving reaction efficiency.

A mole ratio [(b)/(a)] of the content (b) of the reactive functional group σ in the polymer to the content (a) of the specific crosslinked structure in the polymer is preferably 0 to 10, more preferably 0 to 1, and particularly preferably 0 to 0.1, for improving pressure resistance, a dynamic binding capacity to a target substance, and a performance of separating a target substance.

The polymer included in the carrier of the present invention is preferably those having two or more divalent groups formed by ring-opening the cyclic ether group in which the divalent groups form a portion of the specific crosslinked structure, and more preferably those in which the divalent groups form both ends of the specific crosslinked structure.

The polymer included in the carrier of the present invention may have a monovalent group including one or more selected from the group consisting of an ether bond, a thio group, a sulfinyl group, a sulfonyl group, a hydroxyl group, and a sulfanyl group in the molecule, in addition to the above. Such a monovalent group is preferably a group represented by the following Formula (9), a monovalent group containing a sulfanyl group, and a hydroxyl group, and more preferably a group represented by Formula (9) and a monovalent group containing a sulfanyl group.

Examples of the monovalent group containing a sulfanyl group include a sulfanyl group and a group represented by the following Formula (30). When the monovalent group containing a sulfanyl group is contained in the molecule, a ligand such as an antibody can be immobilized by a chemical bond. When the antibody is immobilized in this manner, it becomes useful for, for example, detection and diagnosis of a target substance which binds to an antibody. A ligand such as an antibody can be immobilized by for example, a simple method for reacting a crosslinking agent having a reactive functional group which reacts with a sulfanyl group and a reactive functional group which reacts with a ligand such as an antibody (for example, N-succinimidyl 4-maleimide butyrate):

$$*-Y^4-R^{15}-(-Y^5)_q \qquad (9)$$

wherein
R[15] represents a q+1-valent hydrocarbon group,
Y[4] represents an ether bond, a thio group, a sulfinyl group, or a sulfonyl group,
Y[5] represents a hydrophilic group,
q represents an integer of 0 or more, and
* represents a bond,

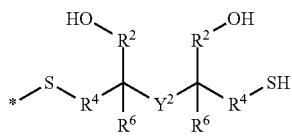
(30)

wherein * represents a bond, and other symbols are as defined above.

In Formula (9), $R^{15}$ represents a q+1-valent hydrocarbon group. That is, when q=0, $R^{15}$ is a monovalent hydrocarbon group, when q=1, $R^{15}$ is a divalent hydrocarbon group, and when q=2, $R^{15}$ is a trivalent hydrocarbon group.

Examples of the monovalent hydrocarbon group represented by $R^{15}$ include the same as the hydrocarbon group represented by $R^5$. Examples of the divalent hydrocarbon group represented by $R^{15}$ include the same as the divalent hydrocarbon group represented by $R^1$. The trivalent hydrocarbon group represented by $R^{15}$ has preferably 1 to 12 carbon atoms, more preferably 1 to 6 carbon atoms. The trivalent hydrocarbon group is preferably an alkanetriyl group such as a methane-1,1,1-triyl group, an ethane-1,1,1-triyl group, an ethane-1,1,2-triyl group, a propane-1,2,3-triyl group, and a propane-1,2,2-triyl group.

In Formula (9), $Y^4$ represents an ether bond, a thio group, a sulfinyl group, or a sulfonyl group, but an ether bond and a thio group are preferred.

Examples of the hydrophilic group represented by $Y^5$ include a hydroxyl group, a sulfanyl group, a carboxyl group, an amino group, and a group forming an organic ammonium salt, and a hydroxyl group is preferred.

q represents an integer of 0 or more, preferably an integer of 0 to 4, and more preferably an integer of 0 to 2. When q is an integer of 2 or more, q $Y^5$s may be the same or different.

A mole ratio of the content (c) of a monovalent group, [(c)/(a)], including one or more selected from the group consisting of an ether bond, a thio group, a sulfinyl group, a sulfonyl group, a hydroxyl group, and a sulfanyl group in the polymer to the content (a) of a specific crosslinked structure in the polymer is preferably 0 to 16, and more preferably 0.1 to 4, for improving pressure resistance, a dynamic binding capacity to a target substance, and a performance of separating a target substance.

Examples of the polymer included in the carrier of the present invention include those in which crosslinking is formed with a specific crosslinked structure between the structural units contained in the polymer and those in which crosslinking is formed by a specific crosslinked structure in the structural unit contained in the polymer, and those in which crosslinking is formed with a specific crosslinked structure between the structural units contained in the polymer is preferred and those which side chains of the structural units contained in the polymer are crosslinked with a specific crosslinked structure is more preferred, for improving pressure resistance, a dynamic binding capacity to a target substance, and a performance of separating a target substance. The polymer included in the carrier of the present invention may have a structural unit (B) having the reactive functional group σ or a structural unit (C) having a monovalent group including one or more selected from the group consisting of an ether bond, a thio group, a sulfinyl group, a sulfonyl group, a hydroxyl group, and a sulfanyl group, in addition to a structural unit (A) which is crosslinked with a specific crosslinked structure.

The structural unit (A) is preferably a structural unit represented by the following Formula (10), the structural unit (B) is preferably a structural unit represented by the following Formula (11), and the structural unit (C) is preferably a structural unit represented by the following Formula (12).

(10)

wherein
$R^{16}$ represents a hydrogen atom or a methyl group,
$R^{17}$ represents a single bond or a divalent linking group, and
** represents a bond which is bonded to the specific crosslinked structure, and means that it is crosslinked with the specific crosslinked structure,

(11)

wherein
$R^{18}$ represents a hydrogen atom or a methyl group,
$R^{19}$ represents a single bond or divalent linking group, and
$Z^1$ represents a reactive functional group σ,

(12)

wherein
$R^{20}$ represents a hydrogen atom or a methyl group,
$R^{21}$ represents a single bond or divalent linking group,
$Z^2$ represents a residue of the reactive functional group σ, and
$Z^3$ represents a monovalent group including one or more selected from the group consisting of an ether bond, a thio group, a sulfinyl group, a sulfonyl group, a hydroxyl group, and a sulfanyl group.

It is preferred that the divalent linking group represented by $R^{17}$ in Formula (10), $R^{19}$ in Formula (11), and $R^{21}$ in Formula (12) is the same as the divalent linking group represented by $Y^1$ in Formula (2). When the two structural units represented by Formula (10) are crosslinked with the crosslinked structure represented by Formula (2), it is preferred that $Y^1$ and $Y^3$ in Formula (2) are a single bond and $R^{17}$ in Formula (10) is a divalent linking group, or $Y^1$ and $Y^3$ in Formula (2) is a divalent linking groups and $R^{17}$ in Formula (10) is a single bond.

The "reactive functional group σ" in $Z^1$ and $Z^2$ is the same as the above reactive functional group σ, and the monovalent group including one or more selected from the group consisting of an ether bond, a thio group, a sulfinyl group, a sulfonyl group, a hydroxyl group, and a sulfanyl group represented by $Z^3$ is the same as the monovalent group including one or more selected from the group consisting of an ether bond, a thio group, a sulfinyl group, a sulfonyl group, a hydroxyl group, and a sulfanyl group described above. Specifically, specific examples of the residue of the reactive functional group σ include a divalent group formed by ring-opening a cyclic ether group, —C(=O)—, and —NH—C(=O)—, and a divalent group formed by ring-opening a cyclic ether group is preferred. When the cyclic ether group is an epoxy group, the divalent group formed by ring-opening a cyclic ether group is a ring-opened epoxy group as represented by —CHOH—CH$_2$—.

The monomer providing the structural units (A) to (C) is preferably a monomer having a reactive functional group σ in the molecule, and more preferably a monomer having a cyclic ether group in the molecule. The monomer may be a non-crosslinkable monomer or a crosslinkable monomer, and may further have a polymerizable functional group other than the reactive functional group σ. Examples of the "polymerizable functional group other than the reactive functional group σ" include a polymerizable unsaturated group.

The number of reactive functional groups σ is preferably 1 to 20, more preferably 1 to 6, still more preferably 1 to 4, and particularly preferably 1 to 2 in one molecule of the monomer. The number of polymerizable functional groups other than the reactive functional group σ is preferably 1 to 10, more preferably 1 to 6, still more preferably 1 or 2, and particularly preferably 1 in one molecule of the monomer.

Examples of the monomer providing the structural units (A) to (C) include a monomer having one cyclic ether group and one polymerizable functional group other than the reactive functional group σ each in the molecule, a monomer having two cyclic ether groups in the molecule but no polymerizable functional group other than the reactive functional group σ, a monomer having two cyclic ether groups and one polymerizable functional group other than the reactive functional group σ each in the molecule, a monomer having two cyclic ether groups and two polymerizable functional groups other than the reactive functional group σ each in the molecule, a monomer having three cyclic ether groups in the molecule but no polymerizable functional group other than the reactive functional group σ, and a monomer having four cyclic ether groups in the molecule but no polymerizable functional group other than the reactive functional group σ. Further, for example, (meth)acrylate-based monomers having an isocyanate group such as isocyanatoethyl (meth)acrylate; unsaturated dicarboxylic anhydride-based monomers such as maleic anhydride, methylmaleic anhydride, and glutaconic anhydride; and also (meta)acrylic acid may be used. These monomers can be used alone or in combination of two or more.

Among these monomers, a monomer having one cyclic ether group and one polymerizable functional group other than the reactive functional group σ each in the molecule is preferred, for improving pressure resistance, a dynamic binding capacity to a target substance, and a performance of separating a target substance.

Examples of the monomer having one cyclic ether group and one polymerizable functional group other than the reactive functional group σ each in the molecule include the same as those described as the "low molecular weight compound having one cyclic ether group and one other polymerizable functional group each in the molecule" which can be used in the method for producing an organic sulfur compound of the present invention, and these may be used alone or in combination of two or more in the reaction.

Examples of the monomer having two cyclic ether groups in the molecule but no polymerizable functional group other than the reactive functional group σ include the same as those described as the "low molecular weight compound having two cyclic ether group in the molecule but no other polymerizable functional group" which can be used in the method for producing an organic sulfur compound of the present invention, and these may be used alone or in combination of two or more in the reaction.

Examples of the monomer having two cyclic ether groups and one polymerizable functional group other than the reactive functional group σ each in the molecule include diglycidyl 4-cyclohexene-1,2-dicarboxylate.

Examples of the monomer having two cyclic ether groups and one polymerizable functional group other than the reactive functional group σ each in the molecule include diglycidyl bicyclo[2.2.1]hepta-2,5-diene-2,3-dicarboxylate.

Examples of the monomer having three cyclic ether groups in the molecule but no polymerizable functional group other than the reactive functional group σ include triglycidyl ethers such as trimethylolpropane triglycidyl ether and glycerol triglycidyl ether (preferably triglycidyl ethers having total 10 to 80 carbon atoms); and triglycidyl isocyanurate, triglycidyl cyanurate, and triglycidyl 1,2,4-benzenetricarboxylate, and these may be used in the reaction alone or in combination of two or more.

Examples of the monomer having four cyclic ether groups in the molecule but no polymerizable functional group other than the reactive functional group σ include tetraglycidyl ethers such as mathanetetrayl tetrakis (glycidylether), sorbitol tetraglycidyl ether, and pentaerytritol tetraglycidyl ether (preferably tetraglycidylethers having total 13 to 80 carbon atoms), and these may be used in the reaction alone or in combination of two or more.

The total content ratio of the structural units (A) to (C) in the polymer is preferably 0 to 100,000 parts by mass, more preferably 10 to 50,000 parts by mass, and particularly preferably 100 to 10,000 parts by mass, with respect to 100 parts by mass of the specific crosslinked structure.

Further, the polymer included in the carrier of the present invention may have a structural unit, in addition to the specific crosslinked structure and the structural units (A) to (C). Examples of the monomer providing such a structural unit (hereinafter, also referred to as other monomers MO2) include a polymerizable unsaturated group-containing monomer having no reactive functional group σ. Other monomers MO2 are roughly classified into a non-crosslinkable monomer and a crosslinkable monomer, and one of these may be used or used in combination.

Examples of the non-crosslinkable monomer include a (meth)acrylate-based non-crosslinkable monomer, a (meth)acrylamide-based non-crosslinkable monomer, an aromatic vinyl-based non-crosslinkable monomer, a vinyl ketone-based non-crosslinkable monomer, a (meth)acrylonitrile-based non-crosslinkable monomer, and an N-vinylamidebased non-crosslinkable monomer. These can be used alone or in combination of two or more. The non-crosslinkable monomer is preferably a (meth)acrylate-based non-crosslinkable monomer and an aromatic vinyl-based non-crosslinkable monomer.

Examples of the (meth)acrylate-based non-crosslinkable monomer, the (meth)acrylamide-based non-crosslinkable monomer, the aromatic vinyl-based non-crosslinkable monomer, the vinyl ketone-based non-crosslinkable monomer, the (meth)acrylonitrile-based non-crosslinkable monomer, the N-vinylamide-based non-crosslinkable monomer include the same as those described as the (meth)acrylate-based non-crosslinkable monomer, the (meth)acrylamide-based non-crosslinkable monomer, the aromatic vinyl-based non-crosslinkable monomer, the vinyl ketone-based non-crosslinkable monomer, the (meth)acrylonitrile-based non-crosslinkable monomer, the N-vinylamide-based non-crosslinkable monomer in "other monomers MO1".

The total content ratio of the structural units providing the non-crosslinkable monomer in the polymer is preferably 1 to 500 parts by mass, more preferably 1 to 100 parts by mass, with respect to 100 parts by mass of the specific crosslinked structure.

Examples of the crosslinkable monomer include a (meth)acrylate-based crosslinkable monomer, an aromatic vinyl-based crosslinkable monomer, and an allyl-based crosslinkable monomer. These can be used alone or in combination of two or more. The crosslinkable monomer is preferably a di- to pentafunctional crosslinkable monomer, and more preferably a di- or trifunctional crosslinkable monomer. Among the crosslinkable monomers, a (meth)acrylate-based crosslinkable monomer and an aromatic vinyl-based crosslinkable monomer are preferred.

Examples of the (meth)acrylate-based crosslinkable monomer, the aromatic vinyl-based crosslinkable monomer, and the allyl-based crosslinkable monomer include the same as those described as the (meth)acrylate-based crosslinkable monomer, the aromatic vinyl-based crosslinkable monomer, and the allyl-based crosslinkable monomer in "other monomers MO1". Further, examples of the crosslinkable monomer include a dehydration condensation reaction product of an amino alcohol such as diaminopropanol, tris(hydroxymethyl)aminomethane, and glucosamine with a (meth)acrylic acid, and a conjugated diolefin such as butadiene and isoprene, in addition to those exemplified above.

The content ratio of the structural units providing the crosslinkable monomer in the polymer is preferably 1 to 1000 parts by mass, more preferably 10 to 500 parts by mass, with respect to 100 parts by mass of the specific crosslinked structure.

Further, the carrier of the present invention may be in any form which can be used as a solid phase carrier. Examples of such a form include a particle shape, a monolith shape, a plate shape, a film shape (including a hollow fiber), a fibrous shape, a cassette shape, and a chip shape, and a particle shape is preferred. The particulate carrier may be magnetic particles to which magnetism is applied or latex particles having a small particle size.

The carrier of the present invention is preferably a porous carrier such as porous particles. The porous particles are preferably porous polymer particles.

When the carrier of the present invention is a particulate carrier, the average particle size (volume average particle size) is preferably 0.01 to 150 µm, more preferably 20 to 100 µm. The variation coefficient of the average particle size is preferably 40% or less, more preferably 30% or less.

The specific surface area of the carrier of the present invention is preferably 1 to 500 $m^2/g$, more preferably 10 to 300 $m^2/g$.

The volume average pore diameter of the carrier of the present invention is preferably 10 to 300 nm.

The average particle size, the variation coefficient, the specific surface area, and the volume average pore size can be measured by, for example, laser diffraction/scattering particle size distribution measurement.

(Ligand)

The carrier of the present invention can be used with or without a ligand other than the specific crosslinked structure being immobilized, but even when the ligand other than the specific crosslinked structure (such as a protein ligand and a peptide ligand) is not immobilized thereon, the carrier has a high dynamic binding capacity to a target substance is large and a high performance of separating a target substance from a biological sample.

When the ligand is used with being immobilized (that is, the ligand-immobilized carrier of the present invention), the ligand other than the specific crosslinked structure may be a molecule which binds to a target substance, and examples thereof include proteins such as protein A, protein G, and avidin; peptides such as insulin; nucleic acids such as DNA and RNA; enzymes; chelate compounds such as iminodiacetic acid; antibodies; antigens; hormones; sugars such as heparin, Lewis X, and gangliosides; receptors; aptamers; vitamins such as biotin and its derivatives; metal ions; synthetic pigments, and also, low molecular weight compounds such as 2-aminophenylboronic acid, 4-aminobenzamidine, and glutathione. The ligand exemplified above may be used as a whole, or a fragment thereof obtained by, for example, recombinant or enzyme treatment may be used. It may also be an artificially synthesized peptide or peptide derivative.

When it is used in immunoassays (immunometric method) such as CLIA and CLEIA, an antibody is preferred as the ligand. On the other hand, when the antibody is used as a target substance, an antibody affinity ligand is usually used, and an immunoglobulin-binding protein is preferred as the antibody affinity ligand. Examples of the antibody affinity ligand include a peptidic ligand, a protein ligand, and a chemically synthetic ligand (synthetic compound). Specific examples thereof include protein A, protein G, protein L, protein H, protein D, protein Arp, protein FcγR, an antibody-binding synthetic peptide ligand, and related substances thereof.

The amount of the ligand other than the specific crosslinked structure immobilized is preferably 0 to 300 mg, more preferably 0 to 150 mg, still more preferably 0 to 75 mg, still more preferably 0 to 25 mg, and particularly preferably 0 to 10 mg, per 1 g of the dry weight of the carrier. The carrier of the present invention has a high dynamic binding capacity to a target substance and a high performance of separating a target substance from a biological sample, even in the case of such a low immobilized amount.

The amount of the ligand other than the specific crosslinked structure immobilized may be measured by, for example, a BCA method, a Bradford method, or a Lowry method.

The ligand may be immobilized on the carrier by a conventional method such as a covalent bond method, an ionic bond method, a physical adsorption method, or an embedding method. Specific examples of the method include a method for binding a ligand to a functional group capable of immobilizing the ligand. This method may be carried out with reference to the descriptions in, for example, the pamphlet of WO 2015/119255 A or the pamphlet of WO 2015/041218 A. More specific examples of the method include a method for binding, for example, a cyclic ether group, a carboxyl group, —C(=O)—O—C(=O), a formyl group of the carrier to, for example, an amino group of the ligand. Further, when the polymer of the carrier has a monovalent group containing a sulfanyl group in the molecule, the ligand can be immobilized using a crosslinking agent having a reactive functional group which reacts with a sulfanyl group such as N-succinimidyl 4-maleimide butyrate and a reactive functional group which reacts with the ligand.

Further, the ligand may be immobilized using, for example, a method for controlling ligand orientation (U.S. Pat. No. 6,399,750, Ljungquist C. et al., rEur. J. Biochem., 1989, Vol. 186, pp. 557-561), a method for immobilizing a ligand on a carrier through a linker (spacer) (U.S. Pat. No. 5,260,373, JP 2010-133733 A, and JP 2010-133734 A), and a method for accumulating a ligand on a carrier by an associative group (JP 2011-256176 A).

<Method for Producing Carrier>

The carrier of the present invention can be produced by appropriately combining conventional methods, but for obtaining a desired carrier safely, efficiently, and by a simple operation, the method for producing a carrier is preferably the following carrier production method PR2-1 and carrier production method PR2-2. Among the carrier production method PR2-1 and the carrier production method PR2-2, the carrier production method PR2-1 is preferred for obtaining a desired carrier safely, efficiently, and by a simple operation.

[Carrier production method PR2-1] A production method including a step of reacting a polymer having a cyclic ether group in the molecule with a compound selected from a thiocarboxylate and a sulfanyl compound having 2 or more groups represented by the following Formula (α) in the molecule.

[Carrier production method PR2-2] A production method including the following steps B-1 and B-2.

(Step B-1) reacting a monomer having a cyclic ether group in a molecule with a compound selected from a thiocarboxylate and a sulfanyl compound having 2 or more groups represented by the following Formula (α) in a molecule, (Step B-2) using a crosslinkable monomer obtained in step B-1 to prepare the carrier:

(α)

wherein $R^2$, $R^4$, $R^6$, and * are as defined above.

—Carrier Production Method PR2-1—

Hereinafter, the carrier production method PR2-1 of the present invention will be described in detail.

(Polymer Having a Cyclic Ether Group in the Molecule)

As the polymer having a cyclic ether group in the molecule used in the carrier production method PR2-1, a commercially available product may be used, or a compound prepared with reference to a known method may be used. Such a polymer can be obtained by, for example, (co)polymerizing a monomer having a cyclic ether group in the molecule. The method of (co)polymerization is preferably suspension polymerization.

Examples of the monomer having a cyclic ether group in the molecule include the same as the monomer having a cyclic ether group in the molecule exemplified as the monomer providing the structural units (A) to (C). Further, other monomers MO2 (non-crosslinkable monomer or crosslinkable monomer) may be copolymerized with the monomer having a cyclic ether group in the molecule.

The total amount of monomers having a cyclic ether group in the molecule used is preferably 1 to 99 parts by mass, more preferably 20 to 95 parts by mass, and particularly preferably 40 to 90 parts by mass, with respect to 100 parts by mass of the total amount of the monomers, for improving pressure resistance, a dynamic binding capacity to a target substance, and a performance of separating a target substance.

The total amount of the non-crosslinkable monomer used is preferably 0 to 50 parts by mass, and more preferably 0.1 to 25 parts by mass, with respect to 100 parts by mass of the total amount of the monomers, for improving pressure resistance, a dynamic binding capacity to a target substance, and a performance of separating a target substance. The total amount of the crosslinkable monomer used is preferably 1 to 70 parts by mass, and more preferably 3 to 60 parts by mass, with respect to 100 parts by mass of the total amount of the monomers, for improving pressure resistance, a dynamic binding capacity to a target substance, and a performance of separating a target substance.

Further, specific examples of the (co)polymerization method include a method in which a polymerization initiator is dissolved in a mixed solution including a monomer and, if necessary, a porosifying agent (monomer solution) and suspended in a water-based medium, and the solution is heated to a predetermined temperature and polymerized, a method in which a polymerization initiator is dissolved in a mixed solution including a monomer and, if necessary, a porosifying agent (monomer solution), and the solution is added to a water-based medium heated to a predetermined temperature and polymerized, and a method in which a mixed solution including a monomer and, if necessary, a porosifying agent (monomer solution) is suspended in a water-based medium and heated to a predetermined temperature, a polymerization initiator is added thereto, and polymerization is carried out.

A radical polymerization initiator is preferred as the polymerization initiator. Examples of the radical polymerization initiator include azo-based initiators, peroxide-based initiators, and redox-based initiators, and specific examples thereof include azobisisobutyronitrile, methyl azobisisobutyrate, azobis-2,4-dimethylvaleronitrile, benzoyl peroxide, di-tert-butyl peroxide, and benzoyl peroxide-dimethylaniline. The total amount of the polymerization initiator used is usually about 0.01 to 10 parts by mass with respect to 100 parts by mass of the total amount of monomers.

The porosifying agent is present with a monomer in polymerization in oil droplets, used for producing porous particles, and has a role of forming pores as a non-polymerizing component. The porosifying agent is not particularly limited as long as it can be easily removed from a porous surface, and examples thereof include a linear polymer soluble in various organic solvents and mixed monomers, and these may be used in combination.

Examples of the porosifying agent include aliphatic hydrocarbons such as hexane, heptane, octane, nonane, decane, and undecane; alicyclic hydrocarbons such as cyclopentane and cyclohexane; aromatic hydrocarbons such as benzene, toluene, xylene, naphthalene, and ethylbenzene; halogenated hydrocarbons such as carbon tetrachloride, 1,2-dichloroethane, tetrachloroethane, and chlorobenzene; aliphatic alcohols such as butanol, pentanol, hexanol, heptanol, 4-methyl-2-pentanol, and 2-ethyl-1-hexanol; alicyclic alcohols such as cyclohexanol; aromatic alcohols such as 2-phenylethylalcohol and benzylalcohol; ketones such as diethylketone, methylisobutylketone, diisobutylketone, acetophenone, 2-octanone, and cyclohexanone; ethers such as dibutylether, diisobutylether, anisole, and ethoxybenzene; esters such as acetateisopentyl, acetatebutyl, acetate-3-methoxybutyl, and diethyl malonate; and also linear polymers such as homopolymers of a non-crosslinkable vinyl monomer. The porosifying agent can be used alone or in combination of two or more.

The total amount of the porosifying agent used is usually about 40 to 600 parts by mass with respect to 100 parts by mass of the total amount of monomers.

Examples of the water-based medium include a water-soluble polymer aqueous solution, and examples of the water-soluble polymer include hydroxyethyl cellulose, polyvinyl alcohol, carboxymethyl cellulose, polyvinyl pyrrolidone, starch, and gelatin.

The total amount of the water-based medium used is usually about 200 to 7000 parts by mass with respect to 100 parts by mass of the total amount of monomers.

When water is used as a dispersion medium of the water-based medium, a dispersion stabilizer such as sodium carbonate, calcium carbonate, sodium sulfate, calcium phosphate, or sodium chloride may be used.

Further, various surfactants including anionic surfactants such as alkyl sulfate ester salts, alkylaryl sulfate ester salts, alkyl phosphate ester salts, and fatty acid salts may be used in the (co) polymerization. Further, nitrites such as sodium nitrite, iodide salts such as potassium iodide, and polymerization inhibitors such as tert-butylpyrocatechol, benzoquinone, picric acid, hydroquinone, copper chloride, and ferric chloride can also be used. Further, a polymerization modifier such as dodecyl mercaptan may be used.

The polymerization temperature may be determined depending on the type of polymerization initiator, but is usually about 2 to 100° C., and when azobisisobutyronitrile is used as the polymerization initiator, the polymerization temperature is preferably 50 to 100° C., and more preferably 60 to 90° C. The polymerization time is usually 5 minutes to 48 hours, preferably 10 minutes to 24 hours.

(Sulfanyl Compound)

The sulfanyl compound having two or more groups represented by Formula (α) in the molecule is preferably those having two groups represented by Formula (α) in the molecule. The two or more Res contained in the sulfanyl compound may be the same or different. The same applies to $R^4$ and $R^6$.

Such a sulfanyl compound is preferably a compound represented by the following Formula (14):

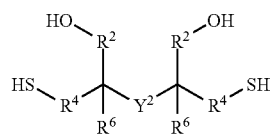

(14)

wherein each symbol in Formula (14) is as defined above.

Examples of the sulfanyl compound include dithiothreitol, dithioerythritol, 1,2-dimercapto-1,2-ethanediol, 2,3-dimercapto-1,4-butanediol, 1,4-dimercaptobutane-2,3-diol, and 3,3'-thiobis(1-mercaptopropane-2-ol). These may be used alone or in combination of two or more in the reaction.

As the sulfanyl compound, a commercially available product may be used, or a compound prepared with reference to a known method may be used.

(Thiocarboxylate)

Examples of the thiocarboxylic acid salt include alkali metal salts such as sodium salts, potassium salts, and lithium salts; salts with Group 2 elements such as calcium salts and magnesium salts; and ammonium salts, pyridinium salts, imidazolium salts, morpholinium salts, pyperidinium salts, pyrrolidinium salts, phosphonium salts, and sulfonium salts. Among these, alkali metal salts are preferred, for efficiently obtaining a desired carrier.

As the thiocarboxylate, those represented by the following Formula (13) are preferred, for obtaining a desired carrier efficiently:

(13)

wherein $R^{22}$ and M are as defined above.

Specific examples of the thiocarboxylate include thioformate, thioacetate, propanethioate, butanethioate, pentanethioate, hexanethioate, octanethioate, nonanethioate, decanethioate, dodecanethioate, and thiobenzoate. Among these, a thioacetate is preferred, and an alkali metal salt of a thioacetic acid is particularly preferred, for efficiently obtaining a desired carrier.

Further, the thiocarboxylate may be used alone or in combination of two or more in the reaction. As the thiocarboxylate, a commercially available product may be used, or a compound prepared with reference to a known method may be used.

The total amount of the compound selected from a thiocarboxylate and a sulfanyl compound having two or more groups represented by Formula (α) in the molecule used is preferably 0.01 mol or more, more preferably 0.05 mol or more, still more preferably 0.1 mol or more, still more preferably 0.25 mol or more, and particularly preferably 0.5 mol or more, with respect to 1 mol of the cyclic ether group, for efficiently obtaining a desired carrier, and preferably 5 mol or less, more preferably 2.5 mol or less, still more preferably 1 mol or less, and particularly preferably 0.75 mol or less, with respect to 1 mol of the cyclic ether group, for efficiently obtaining a desired carrier. When the total amount of the compound selected from a thiocarboxylate and a sulfanyl compound having two or more groups represented by Formula (α) in the molecule used is 0.75 mol or less with respect to 1 mol of the cyclic ether group, a desired carrier can be efficiently obtained.

(Crosslinking Reaction)

Here, the carrier production method PR2-1 of the present invention is to react a compound selected from a thiocarboxylate and a sulfanyl compound having 2 or more groups represented by the following Formula (α) in a molecule with a polymer having a cyclic ether group in the molecule (hereinafter, also simply referred to as "crosslinking reaction"). A carrier in which X is a thio group in Formula (1) can be obtained by the crosslinking reaction.

Further, as illustrated in the following reaction formula, when a thiocarboxylate salt is used, two cyclic ether groups contained in the polymer are ring-opened, and a thio group is introduced therebetween.

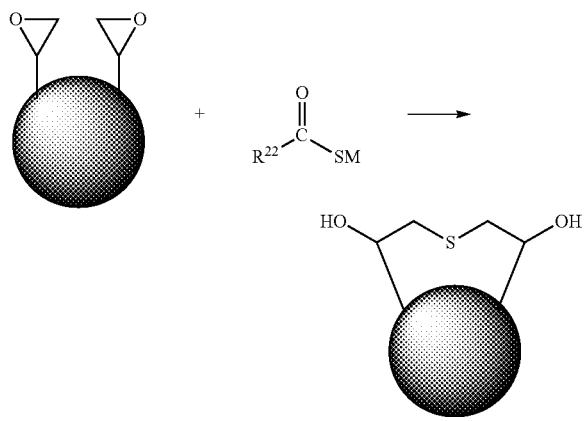

wherein the symbol in the formula is as defined above.

On the other hand, as illustrated in the following reaction formula, when a sulfanyl compound having two or more groups represented by Formula (α) in the molecule is used, the sulfanyl compound acts as a crosslinking agent to ring-open the two cyclic ether groups contained in the polymer, thereby introducing the residue of the sulfanyl compound therebetween.

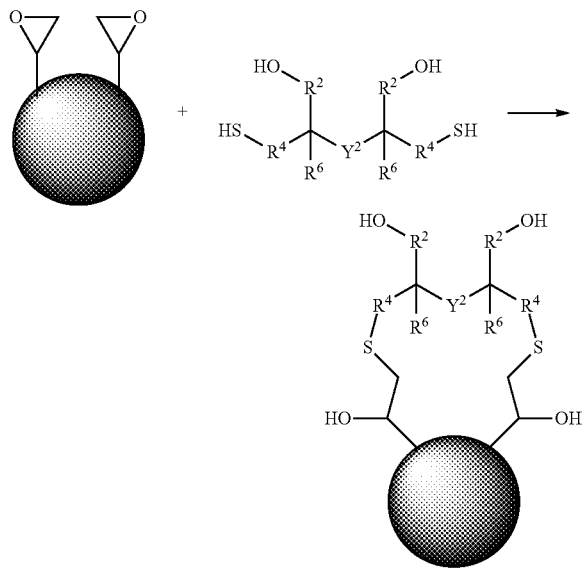

wherein each symbol in the formula is as defined above.

Two divalent groups represented by Formula (1) are contained in the one crosslinked structure of the carrier obtained in the above reaction formula (provided that $R^1$=single bond, $R^3$=—$CH_2$—, $R^5$=hydrogen atom, and X=thio group).

The crosslinking reaction can be carried out in the presence or absence of a solvent, but is preferably carried out in the presence of a solvent, for efficiently obtaining a desired carrier.

Examples of the solvent include the same solvents as those which can be used in the "reaction of introducing a thio group" in the method for producing an organic sulfur compound of the present invention.

The amount of the solvent used is usually 0 to 10,000 parts by mass, but is preferably 10 to 2000 parts by mass, with respect to 100 parts by mass of the polymer having a cyclic ether group in the molecule.

The reaction temperature of the crosslinking reaction is usually 0 to 120° C., preferably 20 to 80° C.

The reaction time of the crosslinking reaction is usually 0.01 to 24 hours, preferably 0.5 to 8 hours.

The reaction pressure of the crosslinking reaction is not particularly limited, and the reaction can be carried out at normal pressure.

When a sulfanyl compound having two or more groups represented by Formula (α) in the molecule is used, the crosslinking reaction may be carried out in the presence of a basic catalyst. Examples of the basic catalyst include triethylamine, N,N-dimethyl-4-aminopyridine, and diisopropylethylamine, and these can be used alone or in combination or two or more.

When a thiocarboxylate is used in the crosslinking reaction, the thiocarboxylate may be present as an ion in a reaction system. Further, it is also included in "reacting the polymer having a cyclic ether group in the molecule with the thiocarboxylate" to create a state in which the thiocarboxylate and its ion are present in the reaction system by, for example, adding a basic substance to the reaction system with the thiocarboxylic acid.

Examples of the reaction conditions for the crosslinking reaction include a basic condition, a neutral condition, and an acidic condition, but when the thiocarboxylate is reacted, it is preferred to carry out the reaction under a neutral to basic condition, for efficiently obtaining a desired carrier. When the thiocarboxylate is reacted, the pH of the crosslinking reaction is preferably 6 or more, more preferably 6 to 14, and particularly preferably 7 to 14, for efficiently obtaining a desired carrier.

Here, the "neutral to basic condition" described above means that a neutral to basic state is created in the reaction system when the polymer having a cyclic ether group in the molecule reacts with the thiocarboxylate, and whether a component other than the polymer having a cyclic ether group in the molecule and the thiocarboxylate (such as a basic substance) is added or not, in the case in which a neutral to basic state is created in the reaction system, it corresponds to a reaction under the "neutral to basic condition" That is, examples of the case "under the neutral to basic condition" include the case in which the inside of the system spontaneously becomes basic by the reaction of the polymer having a cyclic ether group in the molecule with the thiocarboxylate, the case in which a basic substance is attached to make the inside of the reaction system in a range of neutral to basic, and the case in which a state in which a thiocarboxylate and its ion are present in the reaction system by, for example, adding a thiocarboxylic acid to the reaction system with a basic substance instead of the thiocarboxylate is created to make the inside of the reaction system in a range of neutral to basic.

The same applies to pH described above, and for example, "pH 6 or higher" means that a state of pH 6 or higher is created in the reaction system when the polymer having a cyclic ether group in the molecule reacts with the thiocarboxylate, and whether a component other than the polymer having a cyclic ether group in the molecule and the thiocarboxylate (such as a basic substance) is added or not, in the case in which a pH 6 or higher state is created in the reaction system, it corresponds to a reaction under "pH 6 or higher".

—Carrier Production Method PR2-2—

Next, the carrier production method PR2-2 of the present invention will be described.

(Step B-1)

Step B-1 in the carrier production method PR2-2 is a step of reacting a monomer having a cyclic ether group in the molecule with a compound selected from a thiocarboxylate and a sulfanyl compound having two or more groups represented by Formula (a) in the molecule. Step B-1 may be carried out in the same manner as the crosslinking reaction in the carrier production method PR2-1 except that a monomer having a cyclic ether group in the molecule is used instead of the polymer having a cyclic ether group in the molecule. Examples of the monomer having a cyclic ether group in the molecule include the same as the monomer having a cyclic ether group in the molecule exemplified as the monomer providing the structural units (A) to (C).

According to step B-1, a monomer having a cyclic ether group in the molecule and a monomer having a cyclic ether group of a molecule different from the monomer (these monomers may be the same type or different types) can be ring-opened, respectively, to introduce a thio group or the residue of a sulfanyl compound therebetween and connect the two. As illustrated in the following reaction formula, for example, when a monomer having one cyclic ether group and one polymerizable functional group other than the reactive functional group σ each in the molecule is used as the monomer having a cyclic ether group in the molecule, a crosslinkable monomer having two polymerizable functional groups other than the reactive functional group σ in the molecule can be obtained:

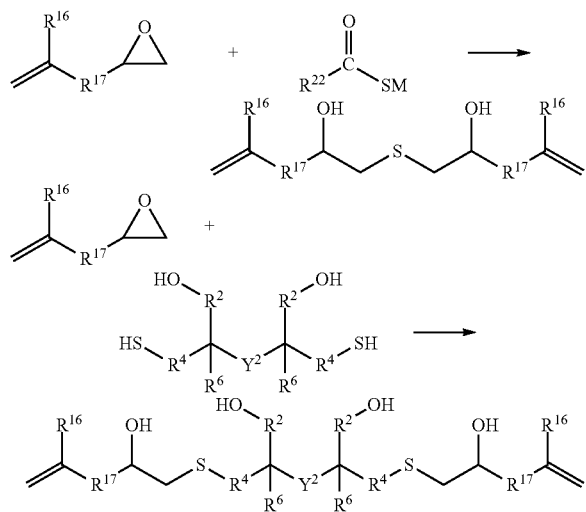

wherein each symbol in the formula is as defined above.

(Step B-2)

Step B-2 in the carrier production method PR2-2 is a step of using a crosslinkable monomer obtained in step B-1 to prepare the carrier. Step B-1 may be carried out in the same manner as preparation of the "polymer having a cyclic ether group in the molecule" in the carrier production method PR2-1, except that the crosslinkable monomer obtained in step B-1 is used instead of the monomer having a cyclic ether group in the molecule.

A carrier in which X is a thio group in Formula (1) can be obtained by step B-2.

When a carrier in which X is a sulfinyl group or a sulfonyl group in Formula (1) is produced, a carrier in which X is a thio group in Formula (1), which is obtained by the crosslinking reaction in the carrier production method PR2-1 or step B-2 in the carrier production method PR2-2, may be oxidized.

The oxidation may be carried out with reference to known methods described in for example, WO 2015/119255 A and JP 2016-50897 A, and specific examples thereof include a method using an oxidizing agent. Examples of the oxidizing agent include organic oxidizing agents such as peracetic acid, perbenzoic acid, metachloroperbenzoic acid, and tert-butyl hydroperoxide; and inorganic oxidizing agents such as hydrogen peroxide, chromic acid, and permanganate. These oxidizing agents can be used alone or in combination of two or more.

When a carrier in which X is an oxy group in Formula (1) is produced, crosslinking between the above cyclic ether groups may be carried out under acid or alkaline conditions, and when a carrier in which X is >N(—$R^{31}$) in Formula (1) may be produced, crosslinking between the cyclic ether groups may be carried out with, for example, a primary or secondary amine. Further, a carrier in which X is >Si(—$R^{32}$)$_2$, >P(—$R^{33}$), >P(=O)(—$R^{34}$), >B(—$R^{35}$), or >C(—$R^{36}$)$_2$ in Formula (1) is produced, crosslinking between the cyclic ether groups may be carried out with a crosslinking agent corresponding to X.

In addition, the cyclic ether group may remain in a product of the crosslinking reaction in the carrier production method PR2-1 or step B-2 in the carrier production method PR2-2 or the carrier after the oxidation, but the remaining cyclic ether group may be ring-opened by a known method. Specific examples of the method include a method for reacting a mercapto group-containing alcohol such as mercaptoethanol or thioglycerol or a polyhydric alcohol such as glycerol with a cyclic ether group.

The product obtained by each of the reactions may be isolated by appropriately combining usual means such as filtration, washing, drying, recrystallization, reprecipitation, dialysis, centrifugation, extraction with various solvents, neutralization, and chromatography as necessary.

Then, the carrier of the present invention which can be produced as described above has excellent pressure resistance, and even when a protein ligand is not immobilized thereon, has a high dynamic binding capacity to a target substance, and has a high performance of separating a target substance from a biological sample. The target substance can be captured without using a capture accelerator such as a lyotropic salt. Further, for example, a bio-related substance such as an antibody can be adsorbed by physical adsorption without using a chemical bond. Furthermore, since the carrier of the present invention can specifically recognize and adsorb an Fc region of an antibody, the carrier has excellent selective separation ability. Further, the carrier can be specifically adsorbed to the Fc region to realize highly oriented antibody adsorption, and as a result, can also be a carrier capable of efficiently recognizing an antigen.

Therefore, the carrier and the ligand-immobilized carrier of the present invention are useful as a chromatography carrier. Further, they are suitable for isolation of a target substance selected from proteins and peptides, and are particularly suitable for protein purification.

In addition, the carrier and the ligand-immobilized carrier of the present invention can also be used for detection and diagnosis of a target substance (for example, immunoassay (immunometric method) such as CLIA and CLEIA), and is useful as a carrier for an in vitro diagnostic agent or a carrier for detecting a bio-related substance in, for example, studies in the field of biochemistry. More specifically, the support portion can be used in an immunoassay as magnetic particles or latex particles, and in ELISA as a substrate, and is useful as a carrier for immunodiagnosis. Examples of the "bio-related substance" which can be detected with the carrier for detecting a bio-related substance include the same target substances as those described later, and specific examples thereof include proteins, peptides, amino acids, sugars, polysaccharides, lipids, vitamins, and nucleic acids (DNA or RNA), and proteins, peptides, and amino acids are particularly preferred.

<Chromatography Column>

In the chromatography column of the present invention, a column container is filled with the carrier or the ligand-immobilized carrier of the present invention.

The chromatography column of the present invention is suitable for isolation of a target substance selected from proteins and peptides, and is particularly suitable for protein purification.

<Method for Detecting or Isolating Target Substance>

The method for detecting or isolating a target substance of the present invention is characterized by using the carrier or the ligand-immobilized carrier of the present invention. Examples of the detection of a target substance include detection by an immunoassay such as a hemagglutination method, a latex agglutination method, a radioimmunoassay, an enzyme immunoassay, a fluorescence immunoassay, and a chemiluminescent immunoassay. The target substance may be detected by referring to, for example, a known method described in JP 2009-031061 A.

Isolation of a target substance includes isolation by chromatography. Further, a target substance can be isolated in the same manner as in known isolation using a protein ligand-immobilized carrier, except that the carrier or the ligand-immobilized carrier of the present invention is used. For example, it may be carried out by referring to a known method described in WO 2015/119255 A.

Examples of the method for isolating a target substance include a method including a step of bringing the carrier or the ligand-immobilized carrier of the present invention into contact with a sample containing a target substance (in the step, it is preferred to use a buffer in a range of pH (at 25° C.) 5 to 10, more preferably pH 6 to 9). In addition, it is preferred to carry out an elution step of eluting the target substance captured in the carrier, after separating impurities from the target substance by the step. In the elution step, a dissociation solution which dissociates a ligand and a target substance is usually used (in the elution step, it is preferred to use a dissociation solution in a range of pH (at 25° C.) 2 to 7, more preferably 3 to 5).

In addition, isolation may be carried out using the chromatography column of the present invention. Examples of the method include a method in which a sample containing a target substance is flowed through the chromatography column of the present invention, and it is preferred to carry out the elution step in the same manner as described above, after separating impurities from the target substance by the step.

Examples of the target substance include bio-related substances such as proteins, peptides, amino acids, sugars, polysaccharides, lipids, vitamins, and nucleic acids (DNA, RNA), but proteins and peptides are preferred, and proteins are more preferred. Examples of the protein to be targeted include antigens, antibodies, Fc fusion proteins, antibody drug conjugates (ADCs), and virus particles, but antigens, antibodies, Fc fusion proteins, and antibody drug conjugates (ADCs) are preferred. Examples of the antibody include a polyclonal antibody, a monoclonal antibody, a bispecific antibody, a synthetic antibody, a humanized antibody, a chimeric antibody, a single chain antibody, a Fab fragment, a Fab' fragment, a F(ab')2 fragment, an Fc fragment, an Fv fragment, an Fv' fragment, a fragment produced by a Fab expression library, an anti-idiotype (anti-Id) antibody, and any of the above epitope-binding fragments. Examples of antibody classes include IgG, IgE, IgM, IgD, and IgA. The subclass is not particularly limited.

Among such proteins, a protein having an Fc region is preferred, and an antibody having an Fc region is more preferred. Specific examples thereof include a polyclonal antibody having an Fc region, a monoclonal antibody having an Fc region, a bispecific antibody having an Fc region, a synthetic antibody having an Fc region, a humanized antibody having an Fc region, a chimeric antibody having an Fc region, an Fc fragment, an anti-idiotype (anti-Id) antibody having an Fc region, any of the above epitope-binding fragments, an Fc fusion protein, and an antibody-drug conjugate (ADC) having an Fc region.

Examples of the sample containing a target substance include blood composition components such as whole blood, serum, plasma, blood components, various blood cells, blood clots, and platelets, body fluids such as urine, semen, breast milk, sweat, interstitial fluid, interstitial lymph, bone marrow fluid, tissue fluid, saliva, gastric fluid, joint fluid, breast water, bile, ascites, and amniotic fluid, and various liquids such as bacterial cell fluid, cell culture medium, cell culture supernatant, and tissue cell disruption fluid.

Examples of impurities include non-target proteins and enzymes. Specifically, when an antibody is used as a target substance, the impurity is a protein or enzyme other than the antibody. When virus particles are used as a target substance, the impurity is DNA or a protein derived from a host cell.

Regarding the above-described embodiment, the present invention further discloses the following production method.

<a1> A method for producing a compound containing a divalent group represented by the following Formula (21), the method including reacting a cyclic ether group-containing compound with a thiocarboxylate:

(21)

wherein
$R^{51}$ and $R^{52}$ independently represent a divalent group in which a cyclic ether group is ring-opened,
$X^2$ represents a thio group, a sulfinyl group, or a sulfonyl group, and
* represents a bond.

<a2> The method described in <a1>, wherein the thiocarboxylate is represented by the following Formula (13):

(13)

wherein
$R^{22}$ represents a hydrogen atom or a monovalent organic group, and

M represents a cation which forms the thiocarboxylate.

<a3> The method described in <a1> or <a2>, wherein the thiocarboxylate is a thioacetate.

<a4> The method described in any one of <a1> to <a3>, wherein the thiocarboxylate is an alkali metal salt of a thioacetic acid.

<a5> The method described in any one of <a1> to <a4>, wherein the cyclic ether group is a cyclic ether group represented by the following Formula (3):

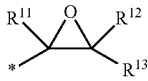

(3)

wherein
$R^{11}$ to $R^{13}$ independently represent a hydrogen atom or an alkyl group, and
* represents a bond.

<a6> The method described in any one of <a1> to <a5>, wherein the reaction is carried out under neutral to basic conditions.

<a7> The method described in any one of <a1> to <a6>, wherein $X^2$ is a thio group.

<a8> The method described in any one of <a1> to <a6>, wherein $X^2$ is a sulfinyl group or a sulfonyl group, and the method further including a step of oxidizing the sulfide compound obtained in the step.

<a9> The method described in any one of <a1> to <a8>, wherein an amount of the thiocarboxylate used is 0.75 mol or less with respect to 1 mol of the cyclic ether group.

<a10> A compound containing a divalent group represented by Formula (21), obtained by the production method described in any one of <a1> to <a9>.

<a11> A compound represented by the following Formula (β):

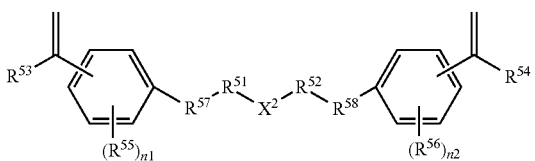

(β)

wherein
$R^{51}$ and $R^{52}$ independently represent a divalent group in which a cyclic ether group is ring-opened,
$R^{53}$ and $R^{54}$ independently represent a hydrogen atom or a methyl group,
$R^{55}$ and $R^{56}$ independently represent a halogen atom or an organic group,
$R^{57}$ and $R^{58}$ independently represent a single bond or a divalent linking group,
$X^2$ represents a thio group, a sulfinyl group, or a sulfonyl group, and
n1 and n2 independently represent an integer from 0 to 4.

<a12> The compound described in <a11>, wherein $R^{51}$ and $R^{52}$ are a ring-opening epoxy group.

<a13> The compound described in <a11> or <a12>, wherein $R^{57}$ and $R^{58}$ are a substituted or unsubstituted divalent hydrocarbon group, or a group in which carbon atoms of the substituted or unsubstituted divalent hydrocarbon group are partially replaced with an ether bond.

<a14> The compound described in any one of <a11> to <a13>, wherein $X^2$ is a thio group.

<b1> A carrier including a polymer having a crosslinked structure containing a divalent group represented by the following Formula (1):

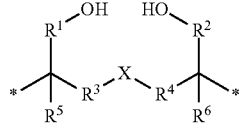

(1)

wherein
$R^1$ to $R^4$ independently represent a single bond or a divalent hydrocarbon group,
$R^5$ and $R^6$ independently represent a hydrogen atom or a hydrocarbon group,
X represents a thio group, a sulfinyl group, a sulfonyl group, an oxy group, >N(—$R^{31}$), >Si(—$R^{32}$)$_2$, >P(—$R^{33}$), >P(=O)(—$R^{34}$), >B(—$R^{35}$), or >C(—$R^{36}$)$_2$ ($R^{31}$ to $R^{36}$ independently represent a hydrogen atom or hydrocarbon group), and
* represents a bond,
with a proviso that when both $R^1$ and $R^3$ are a divalent hydrocarbon group, $R^1$ and $R^3$ may form a ring together with an adjacent carbon atom, and
when both $R^2$ and $R^4$ are a divalent hydrocarbon group, $R^2$ and $R^4$ may form a ring together with an adjacent carbon atom.

<b2> The carrier described in <b1>, wherein $R^1$ to $R^4$ independently are a single bond or a divalent hydrocarbon group having 1 to 10 carbon atoms.

<b3> The carrier described in <b1> or <b2>, wherein $R^1$ and $R^2$ are a single bond, and $R^3$ and $R^4$ independently are a divalent hydrocarbon group having 1 to 10 carbon atoms.

<b4> The carrier described in any one of <b1> to <b3>, wherein $R^1$ and $R^2$ are a single bond, $R^3$ and $R^4$ independently are an alkanediyl group having 1 to 4 carbon atoms, and $R^5$ and $R^6$ are a hydrogen atom.

<b5> The carrier described in any one of <b1> to <b4>, wherein 1 to 5 divalent group(s) represented by Formula (1) is/are contained in the one crosslinked structure.

<b6> The carrier described in any one of <b1> to <b5>, wherein X is a thio group, a sulfinyl group, or a sulfonyl group.

<b7> The carrier described in any one of <b1> to <b5>, wherein X is a thio group.

<b8> The carrier described in any one of <b1> to <b7>, which is a carrier on which a protein ligand is not immobilized.

<b9> The carrier described in any one of <b1> to <b8>, which is a particulate carrier.

<b10> The carrier described in any one of <b1> to <b9>, which is a chromatography carrier, a carrier for an in vitro diagnostic agent, or a carrier for detecting a bio-related substance.

<b11> The carrier described in any one of <b1> to <b9>, which is a chromatography carrier for protein purification.

<b12> A ligand-immobilized carrier having the carrier described in any one of <b1> to <b9> and a ligand, the ligand being immobilized on the carrier.

<b13> The ligand-immobilized carrier described in <b12>, wherein the ligand is an immunoglobulin-binding protein, an antibody or, an antigen.

<b14> A ligand-immobilized carrier described in <b12> or <b13>, wherein a polymer of the carrier has a residue of a monovalent group containing a sulfanyl group in a molecule and the ligand is immobilized on the residue via a linking group derived from a crosslinking agent having a reactive functional group which reacts with a sulfanyl group and a reactive functional group which reacts with the ligand.

<b15> The ligand-immobilized carrier described in any one of <b12> to <b14>, which is a chromatography carrier, a carrier for an in vitro diagnostic agent, or a carrier for detecting a bio-related substance.

<b16> The ligand-immobilized carrier described in any one of <b12> to <b14>, which is a chromatography carrier for protein purification.

<b17> A chromatography column including the carrier described in any one of <b1> to <b16> or a ligand-immobilized carrier with which a column container is filled.

<b18> A method for detecting or isolating a target substance including using the carrier or the ligand-immobilized carrier described in any one of <b1> to <b16>.

<b19> A method for producing the carrier described in any one of <b1> to <b11>, the method including reacting a polymer having a cyclic ether group in a molecule with a compound selected from a thiocarboxylate and a sulfanyl compound having 2 or more groups represented by the following Formula (α) in a molecule:

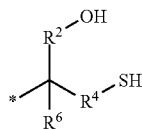

(α)

wherein $R^2$, $R^4$, $R^6$, and * are as defined above.

<b20> A method for producing the carrier described in any one of <b1> to <b11>, the method including the following steps B-1 and B-2.

(Step B-1) reacting a monomer having a cyclic ether group in a molecule with a compound selected from a thiocarboxylate and a sulfanyl compound having 2 or more groups represented by the following Formula (α) in a molecule, (Step B-2) using a crosslinkable monomer obtained in step B-1 to prepare the carrier:

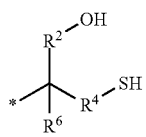

(α)

wherein $R^2$, $R^4$, $R^6$, and are as defined above.

EXAMPLE

Hereinafter, the present invention will be described in detail with reference to the examples, but the present invention is not limited to these examples.

Example 1 Production of Organic Sulfur Compound

Compound (E1) was obtained according to the following synthetic route.

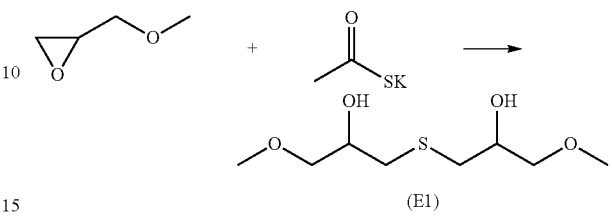

(E1)

That is, in a reaction vessel, 0.50 g of (S)-glycidyl methyl ether (manufactured by Tokyo Chemical Industry Co., Ltd.) was dissolved in 2.5 g of pure water, 0.33 g of potassium thioacetate (manufactured by Tokyo Chemical Industry Co., Ltd.) dissolved in 2.5 g of pure water was dissolved therein, and stirring was performed at room temperature for 4 hours to allow the reaction. As the reaction progressed, the reaction system spontaneously changed from neutral to basic, and then returned to the vicinity of neutral.

After completion of the reaction, it was extracted with ethyl acetate and the solvent was distilled off to obtain a compound (E1) in a yield of 0.55 g.

The obtained compound (E1) was identified by $^1$H-NMR spectrum measurement (device: nuclear magnetic resonance device 600 MHz manufactured by Bruker Corporation).

$^1$H NMR (600 MHz, $D_2O$): δ 2.63 (dd, J=7.8, 13.8 Hz, 2H), 2.75 (dd, J=5.4, 13.8 Hz, 2H), 3.37 (s, 6H), 3.47 (dd, J=6.6, 13.8 Hz, 2H), 3.54 (dd, J=3.6, 10.8 Hz, 2H), 3.94 (m, 2H)

Example 2 Production of Organic Sulfur Compound

Compound (E1) was obtained in a yield of 0.52 g in the same manner as in Example 1, except that the amount of potassium thioacetate used was changed from 0.33 g to 0.65 g.

The obtained compound (E1) was identified by $^1$H-NMR spectrum measurement (device: nuclear magnetic resonance device 600 MHz manufactured by Bruker Corporation).

$^1$H NMR (600 MHz, $D_2O$): δ 2.63 (dd, J=7.8, 13.8 Hz, 2H), 2.75 (dd, J=4.8, 13.8 Hz, 2H), 3.37 (s, 6H), 3.47 (dd, J=6.6, 13.8 Hz, 2H), 3.54 (dd, J=3.6, 10.2 Hz, 2H), 3.94 (m, 2H)

The appearance of each product obtained after all operations of Examples 1 and 2 was confirmed. Further, the yield of compound (E1) in Examples 1 and 2 was calculated. The results are shown in Table 1.

TABLE 1

| | [Amount of potassium thioacetate used (mol)]/[Amount of (S)-glycidyl methyl ether used (mol)] | Yield after extraction purification [%] | Appearance after extraction purification |
|---|---|---|---|
| Example 1 | 0.51 | 91 | Transparent |
| Example 2 | 1.00 | 87 | Turbid |

As shown in Table 1, the production method of Example 1 had a particularly high yield. Further, the appearance of the product was transparent, and it was presumed that there were particularly few by-products.

Example 3 Production of Organic Sulfur Compound

Compound (E2) was obtained according to the following synthetic route.

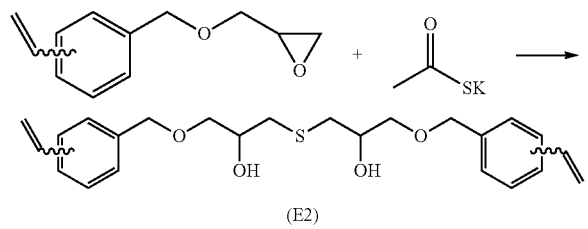

That is, in a reaction vessel, 10.0 g of vinylbenzyl glycidyl ether (a mixture of (3-vinylbenzyl)glycidyl ether and (4-vinylbenzyl)glycidyl ether) was dissolved in a mixed solvent of 17.5 g of pure water and 47.5 g of methanol. Separately, 3.30 g of potassium thioacetate was dissolved in the mixed solvent of 17.5 g of pure water and 47.5 g of methanol, the solution was added to the above reaction vessel, and stirring was performed at room temperature for 4 hours to allow the reaction. As the reaction progressed, the reaction system spontaneously changed from neutral to basic, and then returned to the vicinity of neutral.

After completion of the reaction, it was extracted with ethyl acetate and the solvent was distilled off to obtain a compound (E2) in a yield of 10.80 g.

The obtained compound (E2) was identified by $^1$H-NMR spectrum measurement (device: nuclear magnetic resonance device 600 MHz manufactured by Bruker Corporation).

$^1$H NMR (600 MHz, CDCl$_3$): δ 2.65 (m, 2H), 2.76 (m, 2H), 3.07 (br, 1H), 3.50 (m, 2H), 3.93 (m, 1H), 4.53 (d, J=7.8, 2H), 5.25 (dd, J=8.4, 10.8, 1H), 5.75 (dd, J=10.2, 18.0, 1H), 6.70 (m, 1H), 7.30 (m, 4H)

Example 4 Production of Organic Sulfur Compound

Compound (E3) was obtained according to the following synthetic route. In addition, a large amount of compound (E3) in which p is an integer of 1 to 5 in the formula were obtained.

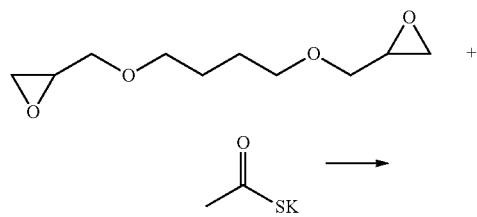

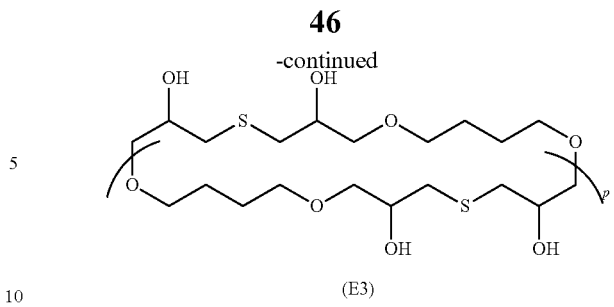

(E3)

That is, in a reaction vessel, 0.115 g of 1,4-butanediol diglycidyl ether (manufactured by Tokyo Chemical Industry Co., Ltd.) was dissolved in a mixed solvent of 0.18 g of pure water and 0.33 g of methanol. Separately, 0.068 g of potassium thioacetate was dissolved in the mixed solvent of 0.18 g of pure water and 0.33 g of methanol, and the solution was added to the above reaction vessel. Stirring was performed at room temperature for 8 hours to allow the reaction. As the reaction progressed, the reaction system spontaneously changed from neutral to basic, and then returned to the vicinity of neutral.

After completion of the reaction, the solvent was removed to obtain the compound (E3).

The obtained compound (E3) was identified by $^1$H-NMR spectrum measurement (device: nuclear magnetic resonance device 600 MHz manufactured by Bruker Corporation) and MALDI-TOF mass measurement (device: AB SCIEX TOF/TOF™ 5800 system).

$^1$H NMR (600 MHz, D$_2$O, CD$_3$OD): δ 1.68 (br s, 4H), 2.66 (m, 2H), 2.94 (m, 2H), 3.51 (m, 8H), 3.88 (m, 2H)

MALDI-TOF mass (Matrix: Dithranol):
p=1[M+Na]$^+$: Found m/z=495.14.
calculated (C20H40O8S2Na) 495.64.
p=2[M+Na]$^+$: Found m/z=731.21.
calculated (C30H60O12S3Na) 731.97.
p=3[M+Na]$^+$: Found m/z=967.30.
calculated (C40H80O16S4Na) 968.29.
p=4[M+Na]$^+$: Found m/z=1203.39.
calculated (C50H100O20S5Na) 1204.62.
p=5[M+Na]$^+$: Found m/z=1439.49.
calculated (C60H120O24S6Na) 1440.95.

Example 5 Production of Organic Sulfur Compound

In a reaction vessel, 1.0 g of triglycidyl isocyanurate (manufactured by Tokyo Chemical Industry Co., Ltd.) was dissolved in a mixed solvent of 1.0 g of pure water and 5.0 g of dimethyl sulfoxide (DMSO). Separately, 0.58 g of potassium thioacetate was dissolved in the mixed solvent of 1.0 g of pure water and 5.0 g of DMSO, the solution was added to the above reaction vessel, and stirring was performed at room temperature. The viscosity gradually increased, and finally a gel with a thickened solvent was formed.

Example 6 Production of Organic Sulfur Compound

In a reaction vessel, 1.93 g of bisphenol A diglycidyl ether (manufactured by Tokyo Chemical Industry Co., Ltd.) was dissolved in 5.0 g of DMSO, 0.65 g of potassium thioacetate dissolved in 5.0 g of DMSO was added thereto, and the mixture was stirred at room temperature. The viscosity gradually increased, and finally a cured product in a state in which the solvent was solidified was formed.

Example 7 Production of Organic Sulfur Compound (1) 2.69 g of polyvinyl alcohol (PVA-217 manufactured by Kuraray Co., Ltd.) was added to 448 g of pure water, polyvinyl alcohol was dissolved by heating and stirring, the solution was cooled, 0.045 g of sodium dodecyl sulfate (manufactured by Wako Pure Chemical Corporation) was added, and stirring was performed to prepare an aqueous solution S.

On the other hand, a monomer composition including 3.63 g of divinylbenzene (manufactured by Wako Pure Chemical Corporation), 0.36 g of 1-ethyl-4-vinylbenzene (manufactured by ChemSampCo, LLC) and 14.15 g of glycidyl methacrylate (manufactured by Mitsubishi Gas Chemical Company, Inc.) was dissolved in 29.38 g of 2-octanone (manufactured by Toyo Gosei Co., Ltd.) to prepare a monomer solution.

Then, the total amount of the aqueous solution S was put into a separable flask, a thermometer, a stirring blade, and a cooling tube were attached thereto, the flask was set in a warm water bath, and stirring was started under a nitrogen atmosphere. The total amount of the monomer solution was put into the separable flask, 1.34 g of 2,2'-azoisobutyronitrile (manufactured by Wako Pure Chemical Corporation) was added when the internal temperature reached 85° C. by heating by the warm water bath, and the internal temperature was brought to 86° C.

(2) Thereafter, stirring was performed for 3 hours while maintaining the temperature at 86° C. Then, after cooling the reaction solution, the reaction solution was filtered and washed with pure water and ethanol. The washed particles were dispersed in pure water and decanted three times to remove small particles. Then, the particles were dispersed in pure water so that the concentration of the particles was 10% by mass to obtain a porous particle dispersion.

(3) Thereafter, 2.51 g of potassium thioacetate was added to 100 g of the porous particle dispersion, and the mixture was stirred at room temperature for 2 hours. As the reaction progressed, the reaction system spontaneously changed from neutral to basic, and then returned to the vicinity of neutral. Then, the reaction solution was filtered and washed with pure water to obtain a porous crosslinked particle dispersion. The reaction in step (3) is shown as follows, and introduction of the crosslinked structure was confirmed by FT-IR measurement and $^1$H-NMR spectrum measurement (device: nuclear magnetic resonance device 600 MHz manufactured by Bruker Corporation, $D_2O$) of an extract by alkaline hydrolysis (5M NaOH).

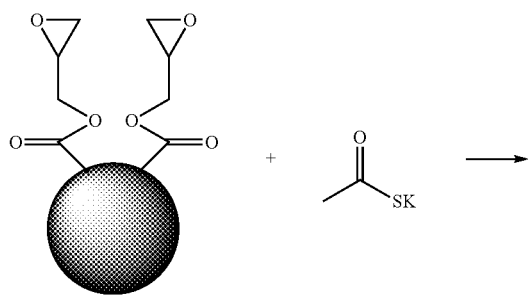

-continued

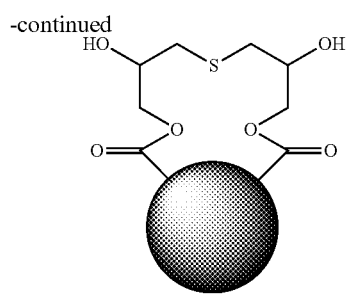

Example 8 Production of Organic Sulfur Compound

A porous crosslinked particle dispersion was obtained in the same manner as in steps (1) to (3) of Example 7.

(4) Then, 47.5 g of α-thioglycerol (manufactured by Tokyo Chemical Industry Co., Ltd.) and 5.67 g of diisopropylethylamine were added to the total amount of the above dispersion, and the mixture was heated to 70° C., maintained at 70° C., and stirred for 3 hours. Thereafter, the reaction solution was filtered and washed with pure water.

(5) Then, 4.06 g of glycerol was added, and the mixture was heated to 70° C. and stirred for 3 hours while being maintained at 70° C. Thereafter, the reaction solution was filtered and washed with pure water. The particles were dispersed in pure water so that the concentration of the particles was 10% by mass to obtain a porous crosslinked particle dispersion.

Example 9 Production of Organic Sulfur Compound

A porous crosslinked particle dispersion was obtained in the same manner as in steps (1) to (3) of Example 7, except that 3.63 g of divinylbenzene was changed to 11.56 g of the compound (E2) obtained in Example 3 in step (1) of Example 7.

Comparative Example 1

The operation was performed in the same manner as in Example 1, except that 0.33 g of potassium thioacetate was changed to 0.22 g of thioacetic acid (manufactured by Tokyo Chemical Industry Co., Ltd.).

After completion of the operation, $^1$H-NMR spectrum measurement (device: nuclear magnetic resonance device 600 MHz manufactured by Bruker Corporation) was performed, but the compound containing a divalent group represented by Formula (21) was not obtained.

$^1$H NMR (600 MHz, $D_2O$): δ 2.39 (s, 3H), 2.95 (dd, J=6.6, 14.4 Hz, 1H), 3.10 (dd, J=5.4, 14.4 Hz, 1H), 3.37 (s, 3H), 3.45 (dd, J=4.2, 10.8 Hz, 1H), 3.49 (dd, J=3.6, 10.2 Hz, 1H), 3.92 (m, 1H)

Example A1 Carrier

A porous crosslinked particle dispersion was obtained in the same manner as in steps (1) to (5) of Example 8. The porous crosslinked particles included in the dispersion are referred to as "chromatography carrier V1".

Example A2 Carrier

A porous crosslinked particle dispersion was obtained in the same manner as in steps (1) to (5) of Example 8, except that 2.51 g of potassium thioacetate was changed to 3.39 g of DL-dithiothreitol and 5.67 g of diisopropylethylamine, and the reaction temperature and reaction time were changed to 70° C. and 3 hours in step (3). The porous crosslinked particles included in the dispersion are referred to as "chromatography carrier V2". The crosslinking reaction using DL-dithiothreitol is shown as follows, and introduction of the crosslinked structure was confirmed by FT-IR measurement and $^1$H-NMR spectrum measurement (device: nuclear magnetic resonance device 600 MHz manufactured by Bruker Corporation, $D_2O$) of an extract by alkaline hydrolysis (5M NaOH).

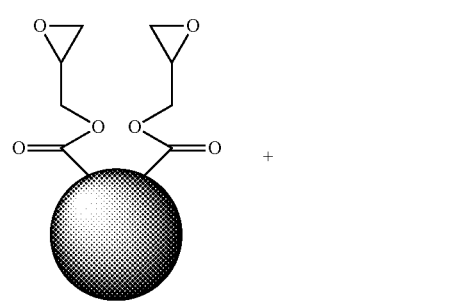

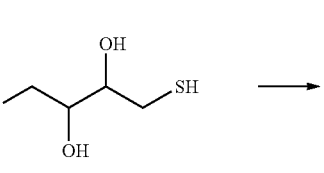

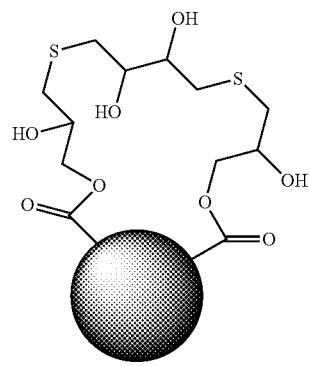

Comparative Example B1

A porous crosslinked particle dispersion was obtained in the same manner as in steps (1) to (5) of Example 8, except that 2.51 g of potassium thioacetate was changed to 4.00 g of 3,6-dithio-1,8-octanedithiol (manufactured by Tokyo Chemical Industry Co., Ltd.) and 5.67 g of diisopropylethylamine, and the reaction temperature and reaction time were changed to 70° C. and 3 hours in step (3). The porous crosslinked particles included in the dispersion are referred to as "chromatography carrier X1". The crosslinking reaction using 3,6-dioxa-1,8-octanedithiol is shown below.

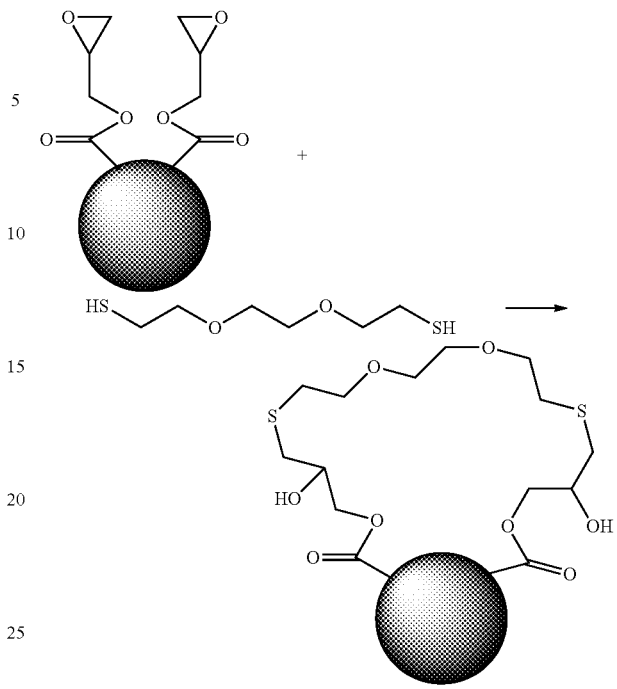

Comparative Example B2

A porous particle dispersion was obtained in the same manner as in steps (1) to (5) of Example 8, except that steps (3) and (5) were not performed. The porous particles included in the dispersion are referred to as "chromatography carrier X2".

Test Example 1-1

Carriers V1, V2, X1, and X2 of each example and comparative example were used in isolation and purification of an antibody without binding protein ligands to evaluate the performance of the carriers. The specific procedure is shown below.

—Equilibration Step—

That is, a column container having a capacity of 1 mL (5 mmφ×50 mm length) was filled with each carrier to a filling height of about 5 cm to manufacture a column. Each of the obtained columns was connected to AKTA Prime Plus manufactured by GE Healthcare, and a 20 mM sodium phosphate/150 mM sodium chloride buffer (pH 7.5) was flowed therethrough at a volume of 4 columns (4 times the column volume) at a linear flow velocity of 300 cm/hr for equilibration.

—Adsorption Step—

Then, a monoclonal antibody Trastuzumab (hereinafter, the monoclonal antibody Trastuzumab is simply referred to as "monoclonal antibody" in each test example) and BSA were dissolved in a 20 mM sodium phosphate/150 mM sodium chloride buffer (pH 7.5), and 100 μL of the sample (monoclonal antibody: 5 g/L, BSA: 5 g/L) was flowed through the column at a linear flow velocity of 300 cm/hr.

—Washing Step—

Then, a 20 mM sodium phosphate/150 mM sodium chloride buffer (pH 7.5) was flowed through the column at a volume of 10 columns at a linear flow velocity of 300 cm/hr to wash the carrier. Whether the monoclonal antibody was contained in the liquid recovered from the column in the washing step was determined by size exclusion chromatography (column: TSKgel UP—SW3000, eluent: 100 mM sodium phosphate (pH 6.7)/100 mM sodium sulfate/0.05% sodium azide, flow velocity: 0.35 ml/min, detection UV: 280 nm), and antibody adsorption performance during washing was evaluated according to the following criteria. The results are shown in Table 2.

(Evaluation Criteria for Antibody Adsorption Performance During Washing)
A: a peak which was determined to be derived from the monoclonal antibody was not confirmed.
B: a peak which was determined to be derived from the monoclonal antibody was confirmed.

—Elution Step—

Thereafter, a 50 mM sodium citrate buffer (pH 3.2) was flowed through the column at a volume of 6 columns at a linear flow velocity of 300 cm/hr to recover an elution fraction of Abs.280>5 mAu.

Then, a spectrophotometer (Bio-Rad SmartSpec Plus spectrophotometer) was used to measure the amount of monoclonal antibody included in the recovered fraction, and an antibody recovery rate (%) was calculated. Furthermore, this antibody recovery rate (%) was evaluated according to the following criteria. The results are shown in Table 2.

(Antibody Recovery Rate Evaluation Criteria)
AA: Antibody recovery rate of 90% or more
A: Antibody recovery rate of 70% or more and less than 90%
B: Antibody recovery rate of 20% or more and less than 70%
C: Antibody recovery rate of less than 20%

Test Example 1-2

A column container having a capacity of 1 mL (5 mmφ× 50 mm length) was filled with carriers V1, V2, X1, and X2 of each example and comparative example to a filling height of about 5 cm to manufacture a column. Each of the obtained columns was connected to AKTA Prime Plus manufactured by GE Healthcare, and a 20 mM sodium phosphate/150 mM sodium chloride buffer (pH 7.5) was flowed therethrough at a volume of 4 columns (4 times the column volume) at a linear flow velocity of 300 cm/hr for equilibration.

Then, BSA was dissolved in a 20 mM sodium phosphate/150 mM sodium chloride buffer (pH 7.5) and 100 μL of the sample (BSA: 5 g/L) was flowed through the column at a linear flow velocity of 300 cm/hr.

Then, a 20 mM sodium phosphate/150 mM sodium chloride buffer (pH 7.5) was flowed through the column at a volume of 10 columns at a linear flow velocity of 300 cm/hr to wash the carrier. A spectrophotometer with AKTA Prime Plus manufactured by GE Healthcare attached was used to measure the absorbance of the liquid. As a result, a peak derived from BSA was confirmed, even when any of carriers V1, V2, X1, and X2 of the examples and the comparative examples was used.

Thereafter, a 50 mM sodium citrate buffer (pH 3.2) was flowed through the column at a volume of 6 columns at a linear flow velocity of 300 cm/hr, and a spectrophotometer with AKTA Prime Plus attached was used to measure the absorbance of the liquid. As a result, a peak derived from BSA was not confirmed, even when any of carriers V1, V2, X1, and X2 of the examples and the comparative examples was used.

Test Example 1-3

A column container having a capacity of 1 mL (5 mmφ× 50 mm length) was filled with carriers V1, V2, X1, and X2 of each example and comparative example to a filling height of about 5 cm to manufacture a column. Each of the obtained columns was connected to AKTA Prime Plus manufactured by GE Healthcare, and a 20 mM sodium phosphate/150 mM sodium chloride buffer (pH 7.5) was flowed therethrough at a volume of 4 columns (4 times the column volume) at a linear flow velocity of 300 cm/hr for equilibration.

Then, the monoclonal antibody was dissolved in a 150 mM sodium chloride buffer (pH 7.5) and 100 μL of the sample (monoclonal antibody: 5 g/L) was flowed through the column at a linear flow velocity of 300 cm/hr.

Then, a 20 mM sodium phosphate/150 mM sodium chloride buffer (pH 7.5) was flowed through the column at a volume of 10 columns at a linear flow velocity of 300 cm/hr, and a spectrophotometer with AKTA Prime Plus manufactured by GE Healthcare attached was used to measure the absorbance of the liquid.

As a result, no peak derived from the monoclonal antibody was confirmed when carriers V1 and V2 of the examples were used. On the other hand, when carriers X1 and X2 of the comparative example were used, a peak derived from the monoclonal antibody was confirmed.

Test Example 1-4

A column container having a capacity of 1 mL (5 mmφ× 50 mm length) was filled with carriers V1, V2, X1, and X2 of each example and comparative example to a filling height of about 5 cm to manufacture a column. Each of the obtained columns was connected to AKTA Prime Plus manufactured by GE Healthcare, and a 20 mM sodium phosphate/150 mM sodium chloride buffer (pH 7.5) was flowed therethrough at a volume of 4 columns (4 times the column volume) at a linear flow velocity of 300 cm/hr for equilibration.

Then, Fc fusion protein Etanercept was dissolved in a 20 mM sodium phosphate/150 mM sodium chloride buffer (pH 7.5) and 100 μL of the sample (Fc fusion protein: 5 g/L) was flowed through the column at a linear flow velocity of 300 cm/hr.

Then, a 20 mM sodium phosphate/150 mM sodium chloride buffer (pH 7.5) was flowed through the column at a volume of 10 columns at a linear flow velocity of 300 cm/hr to wash the carrier. A spectrophotometer with AKTA Prime Plus manufactured by GE Healthcare attached was used to measure the absorbance of the liquid. As a result, no peak derived from Fc fusion protein was confirmed when carriers V1 and V2 of the examples were used. On the other hand, a peak derived from Fc fusion protein was confirmed when carriers X1 and X2 of the comparative examples were used.

Thereafter, a 50 mM sodium citrate buffer (pH 3.2) was flowed through the column at a volume of 6 columns at a linear flow velocity of 300 cm/hr, and a spectrophotometer with AKTA Prime Plus attached was used to measure the absorbance of the liquid. As a result, a peak derived from Fc fusion protein was confirmed when carriers V1 and V2 of the examples were used. On the other hand, no peak derived from Fc fusion protein was confirmed when carriers X1 and X2 of the comparative examples were used.

Test Example 1-5

The operation was performed in the same manner as in Test Example 1-3 except that the monoclonal antibody was changed to lysozyme. As a result, a peak derived from lysozyme was confirmed, even when any of carriers V1, V2, X1, and X2 of the examples and the comparative examples was used.

Further, the operation was performed in the same manner as in Test Example 1-3 except that the monoclonal antibody was changed to albumin (derived from human serum). As a result, a peak derived from albumin (derived from human serum) was confirmed, even when any of carriers V1, V2, X1, and X2 of the examples and the comparative examples was used.

Further, the operation was performed in the same manner as in Test Example 1-3 except that the monoclonal antibody was changed to α-chymotrypsinogen A. As a result, a peak derived from α-chymotrypsinogen A was confirmed, even when any of carriers V1, V2, X1, and X2 of the examples and the comparative examples was used.

Test Example 1-6

Commercially available MAbsorbent A2P HF (manufactured by Prometic Bioseparations) was prepared as a carrier having a non-protein-based synthetic ligand represented by the following formula. The carrier is also referred to as "carrier of Comparative Example B3" and "carrier Y1".

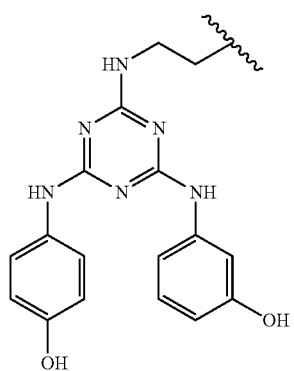 [SMILES: *CCNc1nc(Nc2ccc(O)cc2)nc(Nc2cccc(O)c2)n1]

A column container having a capacity of 1 mL (5 mmφ× 50 mm length) was filled with carrier Y1 to a filling height of about 5 cm to manufacture a column. The obtained column was connected to AKTA Prime Plus manufactured by GE Healthcare, and a 20 mM sodium phosphate/150 mM sodium chloride buffer (pH 7.5) was flowed therethrough at a volume of 4 columns (4 times the column volume) at a linear flow velocity of 300 cm/hr for equilibration.

Then, each of the monoclonal antibody, the Fc fusion protein, BSA, lysozyme, albumin (derived from human serum), and α-chymotrypsinogen A was dissolved in a 150 mM sodium chloride buffer (pH 7.5), and 100 μL of each sample (monoclonal antibody, Fc fusion protein, BSA, lysozyme, albumin (derived from human serum), or α-chymotrypsinogen A: 5 g/L) was flowed through the column at a linear flow velocity of 300 cm/hr.

Then, a 20 mM sodium phosphate/150 mM sodium chloride buffer (pH 7.5) was flowed through the column at a volume of 10 columns at a linear flow velocity of 300 cm/hr, and a spectrophotometer with AKTA Prime Plus manufactured by GE Healthcare attached was used to measure the absorbance of the liquid. As a result, when carrier Y1 of the comparative example was used, even in the case of using any of the monoclonal antibody, the Fc fusion protein, BSA, lysozyme, albumin (derived from human serum), and α-chymotrypsinogen A, a peak therefrom was not confirmed.

Then, the liquid from a 20 mM sodium phosphate/150 mM sodium chloride buffer (pH 7.5) to a 20 mM sodium phosphate/150 mM sodium chloride buffer (pH 5.0) was flowed through the column stepwise every pH 0.5 at a volume of 10 columns at a linear flow velocity of 300 cm/hr, and a spectrophotometer with AKTA Prime Plus manufactured by GE Healthcare attached was used to measure the absorbance of the liquid. As a result, as above, even in the case of using any of the monoclonal antibody, the Fc fusion protein, BSA, lysozyme, albumin (derived from human serum), and α-chymotrypsinogen A, a peak therefrom was not confirmed.

The presence or absence of adsorption when a 20 mM sodium phosphate/150 mM sodium chloride buffer (pH 7.5) was used as the mobile phase in Test Examples 1-2 to 1-6 is summarized in Table 3. The case in which adsorption was observed is designated as "A", and the case in which adsorption was not observed is designated as "B".

Test Example 2 (Measurement of DBC)

AKTA prime plus manufactured by GE Healthcare was used to measure DBC of carriers V1, V2, X1, and X2 of each example and comparative example for a protein (human IgG antibody, HGG-1000 manufactured by Equitech Bio Inc.) at a linear flow velocity of 300 cm/hr. A container having a volume of 4 mL (5 mmφ×200 mm length) was used as a column container and 5 mg/mL of the protein dissolved in 20 mM sodium phosphate/150 mM sodium chloride buffer (pH 7.5) was used as a protein, respectively to determine DBC from the amount of protein captured and the column filling volume at the time of elution tip 10% breakthrough. The results are shown in Table 2.

Test Example 3 (Measurement of Consolidation Linear Flow Velocity)

A column container was filled with carriers V1, V2, X1, and X2 obtained in each example and comparative example to an inner diameter of 16 mm and a filling height of 100 mm, and the column was connected to AKTA pilot manufactured by GE Healthcare Bioscience. Then, pure water was started to flow therethrough at a linear flow velocity of 100 cm/hr, the linear flow velocity was gradually increased by 100 cm/hr every minute, and the linear flow velocity when 2.0 MPa was reached was recorded as a consolidation linear flow velocity. Then, the consolidation linear flow velocity was evaluated according to the following criteria. The results are shown in Table 2.
(Evaluation Criteria for Consolidation Linear Flow Velocity)
A: Consolidation linear flow velocity of 3000 cm/hr or more
B: Consolidation linear flow velocity of less than 3000 cm/hr

TABLE 2

| | | Example A1 | Example A2 | Comparative Example B1 | Comparative Example B2 |
|---|---|---|---|---|---|
| Carrier | Type | V1 | V2 | X1 | X2 |
| | | Crosslinked | Crosslinked | Crosslinked | No Crosslinked |

TABLE 2-continued

|  | | Example A1 | Example A2 | Comparative Example B1 | Comparative Example B2 |
|---|---|---|---|---|---|
| | structure | structure containing divalent group (1) | structure containing divalent group (1) | structure containing no divalent group (1) | crosslinked structure |
| Antibody adsorption performance during cleaning | | A | A | B | B |
| Antibody recovery rate | Measurement | 77% | 93% | 23% | 0% |
| | Evaluation | A | AA | B | C |
| DBC [mg/mL] | | 22 | 17 | 2 | 0 |
| Consolidation linear flow rate | Measurement [cm/hr] | 3900 | 3700 | 3700 | 2200 |
| | Evaluation | A | A | A | B |

TABLE 3

| | | Example A1 | Example A2 | Comparative Example B1 | Comparative Example B2 | Comparative Example B3 |
|---|---|---|---|---|---|---|
| Carrier | Type | V1 | V2 | X1 | X2 | Y1 (*1) |
| | Crosslinked structure | Crosslinked structure containing divalent group (1) | Crosslinked structure containing divalent group (1) | Crosslinked structure containing no divalent group (1) | No crosslinked structure | No crosslinked structure |
| Monoclonal antibody | | A | A | B | B | A |
| Fc fusion protein | | A | A | B | B | A |
| BSA | | B | B | B | B | A |
| Lysozyme | | B | B | B | B | A |
| Albumin (derived from human serum) | | B | B | B | B | A |
| α-chymotrypsinogen A | | B | B | B | B | A |

(*1) MAbsorbent A2P HF (manufactured by Prometic Bioseparations)

As shown in Table 3, carriers V1 and V2 of the examples were adsorbed well to the monoclonal antibody having an Fc region and the Fc fusion protein. Therefore, carriers V1 and V2 of the examples are considered to specifically recognize the Fc region to be adsorbed the monoclonal antibody like protein A, and are presumed to be adsorbed to the antibody or protein having the Fc region.

Further, carriers V1 and V2 of the examples were adsorbed to the monoclonal antibody and the Fc fusion protein, but were not adsorbed to the model proteins (BSA, lysozyme, albumin (derived from human serum), and α-chymotrypsinogen A), and were confirmed to have adsorption selectivity. On the other hand, it was confirmed that carrier Y1 which is commercially available as a carrier having a non-protein-based synthetic ligand was adsorbed to all the samples tested, and lacked the adsorption selectivity.

Test Example 4 Adsorption Rate Test

400 μL of a 20 mM sodium phosphate/150 mM sodium chloride buffer (pH 7.5) containing 0.4 mg of various antibodies shown in Table 4 was added to 20 μL of carriers V1 and V2 of the examples. After incubation for 30 minutes, the supernatant was collected. Then, after washing with 400 μL of a 20 mM phosphate buffer (pH 7.5), the washing liquid was recovered. The total amount of antibody in the supernatant and the washing solution was calculated by measuring the absorbance, and the adsorption rate (%) [=(1−(total amount of antibody in the supernatant and washing solution)/total amount of antibody)×100] was determined from the ratio to the total amount of antibody. Further, after washing, when 400 μL of a 50 mM sodium citrate buffer (pH 3.2) was added, it was confirmed that the antibody was eluted.

TABLE 4

| Carrier | Antibody type | Adsorption rate (%) |
|---|---|---|
| V1 | Monoclonal antibody | 83 |
| | Mouse IgG antibody | 83 |
| | Rabbit IgG antibody | 89 |
| | Rat IgG antibody | 82 |
| V2 | Monoclonal antibody | 69 |
| | Mouse IgG antibody | 76 |
| | Rabbit IgG antibody | 73 |
| | Rat IgG antibody | 68 |

From the results of Test Example 4, it was confirmed that carriers V1 and V2 of the examples were adsorbed to antibodies derived from various animals.

Test Example 5-1 Manufacture of Antibody-Immobilized Particles 1

(1) 50 μL of DMSO in which 47 μg of N-succinimidyl 4-maleimide butyrate was dissolved was added to 20 μL of porous crosslinked particles prepared by performing the operations in the same manner as in steps (1) to (3) of Example 7, and the mixture was allowed to stand at room temperature for 2 hours. The particles were washed 3 times with 400 μL of DMSO to obtain particles to which an N-succinimidyl group was introduced (as a result of quantifying the amount of a sulfanyl group in the particles before and after the reaction using an Elman's reagent, the amount of sulfanyl groups was greatly decreased. This confirmed that the N-succinimidyl group was introduced by the addition reaction of the sulfanyl group on a maleimide site and the particles).

(2) The obtained particles were subjected to solvent replacement twice with 400 μL of a 20 mM sodium phosphate/150 mM sodium chloride buffer (pH 7.5), 400 μL of a 20 mM sodium phosphate/150 mM sodium chloride buffer (pH 7.5) including 1.2 mg of a monoclonal antibody was added, and the mixture was allowed to stand at 4° C. for 15 hours. After recovering the reaction solution, 400 μL each of a 20 mM sodium phosphate/150 mM sodium chloride buffer (pH 7.5), a 50 mM sodium citrate buffer (pH 3.2), a 0.01M sodium hydroxide aqueous solution, and a 20% ethanol aqueous solution was used to perform washing sequentially, thereby obtaining the antibody-immobilized particles.

Test Example 5-2 Manufacture of Antibody-Immobilized Particles 2

Porous crosslinked particle were prepared in the same manner as in steps (1) to (3) of Example 7, except that 2.51 g of potassium thioacetate was changed to 3.39 g of DL-dithiothreitol and 5.67 g of diisopropylethylamine, and the reaction temperature and reaction time were changed to 70° C. and 3 hours in step (3). 50 μL of DMSO in which 106 μg of N-succinimidyl 4-maleimide butyrate was dissolved was added to 20 μL of the porous crosslinked particles, and the mixture was allowed to stand at room temperature for 2 hours. After washing with 400 μL of DMSO 3 times, the operation was performed in the same manner as in step (2) of Test Example 5-1 to obtain antibody-immobilized particles.

From the results of Test Examples 5-1 and 5-2, it was confirmed that the porous crosslinked particles used in Test Examples 5-1 and 5-2 have a sulfanyl group in the molecule of the polymer apart from the specific crosslinked structure, and the particles are physically adsorbed to an antibody, and also when reacted with a crosslinking agent having a reactive functional group reacting with a sulfanyl group and a reactive functional group reacting with an antibody, such as, N-succinimidyl 4-maleimidebutyrate, can immobilize an antibody by a chemical bond, clearly, and thus, can be used as, for example, a carrier for immunodiagnosis.

The invention claimed is:

1. A method for producing a compound comprising a divalent group of formula (21)

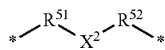

(21)

Wherein $R^{51}$ and $R^{52}$ independently represent-being a divalent group derived from the ring opening of a cyclic ether group, $X^2$ being a thio group, a sulfinyl group, or a sulfonyl group, the method comprising:
reacting a cyclic ether group-containing compound with a thiocarboxylate in the presence of an aqueous solvent having a water content in a range of from 3 to 100% by mass, based on a total mass of the aqueous solvent.

2. The method of claim 1, wherein the thiocarboxylate is of formula (13):

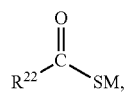

(13)

wherein
$R^{22}$ is H or a monovalent organic group, and
M is a cation which forms the thiocarboxylate.

3. The method of claim 1, wherein the thiocarboxylate is a thioacetate.

4. A compound comprising a divalent group of formula (21), obtained by the method of claim 1.

5. The method of claim 1, wherein the water content of the aqueous solvent is in a range of from 20 to 100% by mass, based on the total mass of the aqueous solvent.

6. The method of claim 1, wherein the aqueous solvent is present in the reacting in a range of from 10 to 2000 parts by mass, with respect to 100 parts by mass of the compound comprising the cyclic ether group.

7. The method of claim 1, wherein the thiocarboxylate is present in the reacting in a range of from 0.01 to 5 mol., with respect to 1 mol. of the cyclic ether group.

8. The method of claim 1, wherein the compound comprising the divalent group of formula (21) has a formula (B):

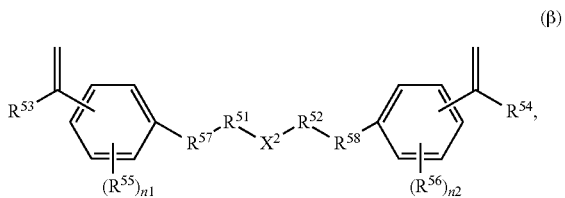

(β)

wherein
$R^{51}$ and $R^{52}$ are independently a divalent group formed by ring-opening of a cyclic ether group,
$R^{53}$ and $R^{54}$ are independently H or a methyl group,
$R^{55}$ and $R^{56}$ are independently a halogen atom or an organic group,
$R^{57}$ and $R^{58}$ are independently a single bond or a divalent linking group,
$X^2$ is a thio group, a sulfinyl group, or a sulfonyl group, and
n1 and n2 are independently an integer in a range of from 0 to 4.

9. The method of claim 8, wherein, in the formula (B), $R^{53}$ and $R^{54}$ are a methyl group.

* * * * *